US006593080B1

(12) United States Patent
Smith

(10) Patent No.: US 6,593,080 B1
(45) Date of Patent: Jul. 15, 2003

(54) DIAGNOSIS, PREVENTION AND TREATMENT OF CALICIVIRUS INFECTION IN HUMANS

(75) Inventor: Alvin W. Smith, Corvallis, OR (US)

(73) Assignee: The State of Oregon Acting by and through the State Board of Higher Education on Behalf of Oregon State University, Corvallis, OR (US)

( * ) Notice: Subject to any disclaimer, the term of this patent is extended or adjusted under 35 U.S.C. 154(b) by 0 days.

(21) Appl. No.: 09/496,320

(22) Filed: Feb. 1, 2000

Related U.S. Application Data

(60) Provisional application No. 60/118,209, filed on Feb. 1, 1999.

(51) Int. Cl.[7] .......................... C12Q 1/70; C12Q 33/59; C07K 17/00

(52) U.S. Cl. ............................. 435/5; 435/7.1; 530/350

(58) Field of Search .............................. 530/350; 435/5, 435/7.1, 235.1; 424/186.1, 216.1

(56) References Cited

PUBLICATIONS

Neill. Virus Research. 1992; 24: 211–222.*
Berry et al. 1987. ASM Annual Meeting, Mar. 1–6. Atlanta, GA. Abstract.*
Bradley. 1995. Journal of Hepatology. vol. 22 (Suppl. 1), pp. 140–145.*
Soergel et al. 1978. Archives of Virology. vol. 57. No. 3. Abstract only.*

Nakata et al. Journal of Clinical Microbiology. 1983; 17: 198–201.* sequence aligment of SEQ ID No.: 5 with Neill. Virus Research 1992; 24: 211–222, PIR_68 database. Accession No: C48562.*

Neill et al. May 1, 1997. Sequence retreival from Genbank accession No. P89669.*
Smith et al., "In Vitro Isolation and Characterization of a Calicivirus Causing a Vesicular Disease of the Hands and Feet," *Clinical Infectious Diseases*, 26:424–439, 1998.
Berry et al., "Marine Calicivirus Disease in Man: The First Documented Case," Abstract, *1987 ASM Annual Meeting*, Mar. 1–6, 1987, Atlanta, GA.
Poet, Steven E., "Development and Diagnostic Applications of a Group–Specific Caliciviridae cDNA Hybridization Probe Cloned from San Miguel Sea Lion Virus, Type 5, a Calicivirus of Ocean Origin," Thesis presented Mar. 25, 1994.
Smith et al., "Calicivirus Infecting Monkeys and Possibly Man," *Amer. J. Vet. Res.*, 39(2): 287–289, Feb. 1978.
Smith et al., "Calicivirus Emergence from Ocean Reservoirs: Zoonotic and Interspecies Movements," *Emerging Infectious Diseases*, 4(1):13–20, Jan.–Mar. 1998.
Smith et al., "Host Range Comparisons of Five Serotypes of Calicivirus," *Amer. J. Vet. Res.*, 38(1):101–105, Jan. 1977.
Smith et al., "Calicivirus Isolation and Persistence in a Pygmy Chimpanzee (*Pan paniscus*)," American Assoc. for Advancement of Science, 221:79–81, Jul. 1, 1983.

* cited by examiner

*Primary Examiner*—James Housel
*Assistant Examiner*—Shanon Foley
(74) *Attorney, Agent, or Firm*—Klarquist Sparkman, LLP

(57) ABSTRACT

Caliciviruses are herein recognized as potentially important human pathogens, infecting a large percentage (18%) of a sampled human population. A new calicivirus isolate called "San Miguel sea lion virus 5 serotype *Homosapien*-1" (SMSV-5 Hom-1) is also disclosed. Compositions and methods are disclosed that allow diagnosis, prevention and treatment of calicivirus (including SMSV-5 Hom-1) infection in humans.

13 Claims, 23 Drawing Sheets

```
                    10         20         30         40         50         60
SMSV-5     TGGATGGGCCTGCAGTCGAGGATCTCTTCAAAAGGCTGGAAAAACCTAGGCACGACCGGT
           AspGlyProAlaValGluAspLeuPheLysArgLeuGluLysProArgHisAspArg
Hom-1      ------------------------------------------------------------

Pan-1      ----C--A------T--T--A--------------------C---CG---A-A------T----
                                                        Arg  Lys

SMSV-5     ATTGTGTTGACTACTCCAAGTGGGATTCAACTCAGCCACCAAAAGTTACATCCCAATCAA
           IleCysValAspTyrSerLysTrpAspSerThrGlnProProLysValThrSerGlnSer
Hom-1      ------------------------------------------------------------

Pan-1      ----------------A---------C-----C--A-----------A------------

SMSV-5     TTGACATCCACAGGCACTTCACTGACAAATCTCCAATTGTTGATTCGGCCTGTGCACGAC
           IleAspIleHisArgHisPheThrAspLysSerProIleValAspSerAlaCysAlaArg
Hom-1      ---G---A-T----------------------------------------TAC--
           Gly  Leu                                          Thr
Pan-1      --------T---------T------------------------A-----GC--
              Leu                                              Ala

SMSV-5     TCAAATCAAACCCAGTTGGCATCTTCAATGGCGTGGCGTTTAAGGTTGCGGGTGGACTAC
           LeuLysSerAsnProValGlyIlePheAsnGlyValAlaPheLysValAlaGlyGlyLeu
Hom-1      ----G---G----------------------------------------C--
               Ser                                          Pro
Pan-1      --------------A-C--A--T---------T--T--A--C-----G--T-----GT-G-
                   Ile

SMSV- 5    CGTCTGGTATGCCACTCACTTCCATCATCAACTCACTGAATCACTGTCTCATGGTAGGCT
           ProSerGlyMetProLeuThrSerIleIleAsnSerLeuAsnHisCysLeuMetValGly
Hom-1      ------------------------------------------------------------
Pan-1      -T--G------T----G--A--------------G--C---------C--------G----
                      Ser

SMSV-5     GTGCTGTCACTAAGGCTCTCGAGGACTCAGGCGTGCAGGTGACTTGGAACATCTTCGATT
           CysAlaValThrLysAlaLeuGluAspSerGlyValGlnValThrTrpAsnIlePheAsp
Hom-1      -----------------------------------------------------------C-
Pan-1      CA-----TGTC-----A-----------T--------A-----A--------------C-
           Ser     Val

SMSV-5     CGATGGACCTGTTTACCTATGGTGACGACGGTGTCTACATCGTCCCACCTCTCATCTCTT
           SerMetAspLeuPheThrTyrGlyAspAspGlyValTyrIleValProProLeuIleSer
Hom-1      ------------------------------------------------------------
Pan        ----------A--C--A--------T-----G-----------------A-----A--A-

SMSV-5     CTGTCATGCCCAAAGTCTTTGCGAACCTGAAAC
           SerValMetProLysValPheAlaAsnLeuLys
Hom-1      -------------------------ACG--
                                    Arg
Pan-1      ------------------CA-C----------
                             Thr
```

FIG. 4

| | | | | |
|---|---|---|---|---|
| 1 | aaaagattta | aagataaatg | gtgaattggc | tactttcagg | ctgaacagca |
| 51 | ccctcccaac | tgctgttcca | gtcggaacat | ccaaacccat | taaggaccca |
| 101 | tggggaaacc | cagtgtccac | agattggcaa | ttcaaagaat | ttaacaccac |
| 151 | atctggacac | atctatggtg | cttcagcatc | atcctgttcc | ttaacccgcc |
| 201 | aggtgattgt | gggctaccat | acaccgacga | acacggtgtt | gtggtgggcc |
| 251 | tgcatgcggg | atcgGgTgGt | GACAAGTGCC | CCTCGCGTAA | ACTCGTCGTA |
| 301 | CCTTACGTTA | AGGTCGACAT | GAAGATTCGC | GACACGTGCA | CAAAGGAGTA |
| 351 | CTACAAGGAC | AATCAACCAA | TCATTTCTTA | CAAAGGACTG | CTGGTAAAGG |
| 401 | AAACAGGGGA | TCCAAGAACT | ATCATGAAGG | AACGCGACT | CCACGTATCA |
| 451 | CCCGCTCACA | CGGGTGACTA | CGAGGAGTGC | TCCCATCAAC | CAGCCTCTTT |
| 501 | GGGTGCAGGG | GATCCAAGAT | GTCCCATTTC | CCTCACCGGG | ATCATGGTAA |
| 551 | ACAACCTGCA | ACCATACACA | GAGGCAGCTC | CTGGACCAGA | CACCAGCACA |
| 601 | CTCAACCGAG | TGTCGAAAAT | GCTGACTACC | CACATGGAAG | GCTACGTGCC |
| 651 | CAAAGTCCAC | AAAACTGAGG | AAGACATGCT | TTCGGCATTC | TACATGCTGA |
| 701 | ATCATGACAC | ATCCTGCGGC | CCTTACATCG | GCGGCCGGAA | AAAAGACCAT |
| 751 | GTTAAGGACG | GTGTCCTAGA | TAAGGCCTTG | CTGGACCTCC | TCAGTTCAAA |
| 801 | ATGGAACCGT | GCTAAACTGG | GCTTAGCTCT | ACCACACGAG | TATGCCCTCG |
| 851 | GCCTCAAAGA | TGAACTTCGA | CCAAAAGACA | AAGTCGCCGT | TGGTAAGCGC |
| 901 | AGGTTGATCT | GGGGCTGCGA | TGTTGGCGTT | AGCACTGTCT | GTGCTGCTGC |
| 951 | CTTCAAGCGC | GTCTCGGAGT | CAATCATGGC | AAACCACGCG | TTAGGTTTCA |
| 1001 | TCCAAGTTGG | CATCAACATG | GATGGGCCTG | CAGTCGAGGA | TCTCTTCAAA |

FIG. 6A

```
1051    AGGCTGGAAA AACCTAGGCA CGACCGGTAT TGTGTTGACT ACTCCAAGTG

1101    GGATTCAACT CAGCCACCAA AAGTTACATC CCAATCAATT GACATACTCA

1151    GGCACTTCAC TGACAAATCT CCAATTGTTG ATTCGGCCTG TGCTACGCTC

1201    AAGTCAAACC CAGTTGGCAT CTTCAATGGC GTGGCGTTTA AGGTTGCGGG

1251    TGGACTACCG TCTGGTATGC CACTCACTTC CATCATCAAC TCACTGAATC

1301    ACTGTCTCAT GGtAGGCTGT GCTGTCACTa AgGCTCTCGA GGACTCAGgC

1351    GTGCAGGTGA CTTGGAACAT CTTCGACTCG ATGGACCTGT TTACCTATGG

1401    TGACgACGGT GTCTACATCg TCCcAcctCt catctcttct gtcatgccca 1451    aagtctttgc gaacctacga cagttcggcc tgaaaccgac ccggaccgat 1501    aaaacggatg ctgagataac gcccatccct gcagatgaac cagttgagtt 1551    tctcaaacga acacttgtcc gaactgagaa tggcatacga gcacttctgg 1601    acaaatcctc aataattcgg cagttctact acatcaaagc agagaacacc 1651    gaggaatgga ccaaaccgcc a
```

FIG. 6B

```
AAAGATTAAAGATAAATGGTGAATTGGCTACTTTCAGGCTGAACAGCACCCTCCCAACTGCTGTTCCA
TTTCTAAATTTCTATTTACCACTTAACCGATGAAAGTCCGACTTGTCGTGGGAGGGTTGACGACAAGGT
0b                    20b                    40b                    60b
        Lys Ile ... Arg ... Met Val Asn Trp Leu Leu Ser Gly ... Thr Ala Pro Ser Gln Leu Leu Phe Gln
        Lys Asp Leu Lys Ile Asn Gly Glu Leu Ala Thr Phe Arg Leu Asn Ser Thr Leu Pro Thr Ala Val Pro
        Lys Arg Phe Lys Asp Lys Trp ... Ile Gly Tyr Phe Gln Ala Glu Gln His Pro Pro Asn Cys Cys Ser

GTCGGAACATCCAAACCCATTAAGGACCCAGTGGGAAACCCAGTGTCCACAGATTGGCAATTCAAAGAAT
CAGCCTTGTAGGTTTGGGTAATTCCTGGGTACCCTTTGGGTCACAGTGTCTAACCGTTAAGTTTCTTA
                  80b                    100b                   120b                   140b
  Ser Glu His Pro Asn Pro Leu Arg Thr His Gly Glu Thr Gln Cys Pro Gln Ile Gly Asn Ser Lys Asn
  Val Gly Thr Ser Lys Pro Ile Lys Asp Pro Trp Gly Asn Pro Val Ser Thr Asp Trp Gln Phe Lys Glu
  Ser Arg Asn Ile Gln Thr His ... Gly Pro Met Gly Lys Pro Ser Val His Arg Leu Ala Ile Gln Arg

TTAACACCACACTCTGGACACATCTATGGTGCTTCAGCATCATCCTGTTCCTTAACCCGCCAGGTGATTGT
AATTGTGTGTAGACCTGTGTAGATACCACGAGTCGTAGTAGGACAAGGAATTGGGCGGTCCACTAACA
                 160b                   180b                   200b
    Thr Pro His Leu Asp Thr Ser Met Val Leu Gln His His Pro Val Pro ... Pro Ala Arg ... Leu Trp
    Asn Thr Thr Ser Gly His Ile Tyr Gly Val Ala Ser Ala Ser Ser Cys Ser Leu Thr Arg Gln Val Ile Val
    ... His His Ile Trp Thr His Leu Trp Cys Phe Ser Ile Ile Leu Phe Leu Asn Pro Pro Gly Asp Cys

GGGCTACCATACACCGACGAACACGGTGTTGTGGGCCTGCATGCGGATCGGTGGTGGTGACAAGTGCC
CCCGATGGTATGTGGCTGCTTGTGCCACAACACCGGACGTACGCCTAGCCACCACTGTTCACGG
                 220b                   240b                   260b                   280b
  Ala Thr Ile His Arg Arg Thr Arg Cys Cys Gly Gly Pro Ala Cys Gly Ile Gly Trp ... Gln Val Pro
  Gly Tyr His Thr Pro Asn Thr Val Leu Trp Trp Ala Cys Met Arg Asp Arg Val Val Thr Ser Ala
  Gly Leu Pro Tyr Thr Asp Val Gly Leu His Ala Gly Ser Gly Val Gly Asp Cys
```

FIG. 7A

CCTCGCGTAAAC~CGTCGTkCCTTACGTTAAGGTCGACATGAAGATTCGCGACACGTGCACAAAGGAGTA
GGAGCGCATTTGAGCAGCAGCAATGAATGCAATTCCAGCTGTACTTCTAAGCGCTGTGCACGTGTTCCTCAT
                    300b                                      320b                                        340b

Leu Ala ... Thr Arg Arg Thr Leu Arg ... Gly Arg His Glu Asp Ser Arg His Val His Lys Gly Val
Pro Arg Val Asn Ser Ser Tyr Leu Thr Leu Arg Ser Thr ... Arg Phe Ala Thr Arg Ala Gln Arg Ser
Pro Ser Arg Lys Leu Val Val Pro Tyr Val Lys Val Asp Met Lys Ile Arg Asp Thr Cys Thr Lys Glu

CTACAAGGACAATCAACCAATCATTCTTACAAAGGACTGCTGGTAAAGGAAACAGGGGATCCAAGAACT
GATGTTCCTGTTAGTTGGTTAGTAAAGAATGTTTCCTGACGACCATTTCTTTGTCCCCTAGGTTCTTGA
                    360b                                      380b                                        400b                                  420b

Gln Gly Gln Ser Asn His Phe Leu Gln Arg Thr Ala Gly Lys Gly Asn Arg Gly Ser Lys Asn Tyr
Thr Arg Thr Ile Asn Gln Ser Phe Leu Thr Lys Asp Cys Trp ... Arg Lys Gln Gly Ile Gln Glu Leu
Tyr Lys Asp Asn Gln Pro Ile Ile Ser Tyr Lys Leu Val Lys Glu Thr Gly Asp Pro Arg Thr

ATCATGAAGGGAACGCGACTCCACGTATCACCCGCTCACACGGGTGACTACGAGGAGTGCTCCCATCAAC
TAGTACTTCCCTTGCGCTGAGGTGCATAGTGGGCGAGTGTGCCACTGACTGATGCTCCTCACGAGGGTAGTTG
                    440b                                      460b                                        480b

His Glu Gly Asn Ala Thr Pro Arg Ile Thr Arg Ser His Gly ... Leu Arg Gly Val Leu Pro Ser Thr
Ser ... Arg Glu Arg Asp Ser Thr Tyr His Pro Leu Thr Arg Val Thr Thr Arg Ser Ala Pro Ile Asn
Ile Met Lys Gly Thr Arg Leu His Val Ser Pro Ala His Thr Gly Asp Tyr Glu Cys Ser His Gln

CAGCCCTCTTTGGGTGCAGGGGATCCAAGATGTCCCATTTCCCTCACCGGGATCATGGTAAACAACCTGCA
GTCGGAGAAACCCACGTCCCCTAGGTTCTACAGGGTAAAGGGAGTGGCCCTAGTAGTACCATTTGTTGACGT
                    500b                                      520b                                        540b                                  560b

Ser Leu Phe Gly Cys Arg Gly Ser Lys Met Ser His Phe Pro His Arg Asp His Gly Lys Gln Pro Ala
Gln Pro Leu Trp Val Gln Gly Ile Gly Ile Gln Asp Val Pro Phe Pro Ser Pro Gly Ser Trp ... Thr Thr Cys
Pro Ala Ser Leu Gly Ala Gly Asp Pro Arg Cys Pro Ile Ser Leu Thr Gly Ile Met Val Asn Asn Leu

FIG. 7B

```
ACCATACACAGAGGCAGCTCCTGGACCAGACACCAGCACACTCAACCGAGTGTCGAAAATGCTGACTACC
TGGTATGTGTCCGTCCGAGGACCTGGTCTGTGGTCGTGTGAGTTGGCTCACAGCTTTTACGACTGATGG
                              580b                                  620b

Ile His Arg Gly Ser Ser Trp Thr Arg His Gln His Thr Gln Pro Ser Val Glu Asn Ala Asp Tyr Pro
His Thr Gln Arg Gln Leu Leu Asp Gln Thr Pro Ala His Ser Thr Glu Cys Arg Lys Cys ... Leu Pro
Pro Tyr Thr Glu Ala Ala Pro Gly Pro Asp Thr Ser Thr Leu Asn Arg Val Ser Lys Met Leu Thr Thr

CACATGGAAGGCTACGTGCCCAAAGTCCACAAAACTGAGGAAGACATGCTTTCGGCATTCTACATGCTGA
GTGTACCTTCCGATGCACGGTTTCAGTGTTTTGACTCCTTCTGTACGAAAGCCGTAAGATGTACGACT
                       640b                               660b                     680b     700b

His Gly Arg Leu Arg Ala Gln Ser Pro Gln Asn ... Gly Arg His Ala Phe Gly Ile Leu His Ala Glu
Thr Trp Lys Ala Thr Cys Pro Lys Ser Thr Lys Leu Arg Lys Thr Cys Phe Arg His Ser Thr Cys ...
His Met Glu Gly Tyr Val Pro Lys Val His Lys Thr Glu Glu Asp Met Leu Ser Ala Phe Tyr Met Leu

ATCATGACACATCCTGCGGCCCTTACATCGGCGCCGGGAATGTAGCGCCGGCCTTTTTCTGGTACAATTCCTGCCACAGGATCT
TAGTACTGTGTAGGACGCCGGGAATGTAGCGCCGGCCTTTTTCTGGTACAATTCCTGCCACAGGATCT
                720b                                     740b                 760b

Ser ... His Ile Leu Arg Pro Leu His Arg Arg Pro Glu Lys Arg Pro Cys ... Gly Arg Cys Pro Arg
Ile Met Thr His Pro Ala Ala Leu Thr Ser Ala Ala Gly Lys Lys Thr Met Leu Arg Thr Val Ser ...
Asn His Asp Thr Ser Cys Gly Pro Tyr Ile Gly Arg Lys Lys Asp His Val Lys Asp Gly Val Leu

TAAGGCCTTGCTGGACCTCCTCAGTTCAAAATGGAACCGTGCTAAACTGGGCTTAGCTCTTACCACACGAG
ATTCCGGAACGACCTGGAGGAGTCAAGTTTTACCTTGGCACGATTTGACCCGAATCGAGATGGTGTGCTC
                780b                          800b                      820b           840b

Gly Leu Ala Gly Pro Pro Gln Phe Lys Met Glu Pro Cys ... Thr Gly Leu Ser Ser Thr Thr Arg Val
Arg Pro Cys Trp Thr Ser Ser Val Gln Asn Gly Thr Val Leu Asn Trp Ala ... Leu Tyr His Thr Ser
Lys Ala Leu Leu Asp Leu Leu Ser Ser Lys Trp Asn Arg Ala Lys Leu Gly Leu Ala Leu Pro His Glu
```

FIG. 7C

```
TATGCCCTCGGCCTCAAAGATGAACTTCGACCAAAAGACAAAGTCGCCGTTGGTAAGCGCAGGTTGATCT
ATACGGGAGCCGGAGTTTCTACTTGAAGCTGGTTTTCTGTTTCAGCGGCAACCATTCGCGTCCAACTAGA
                     860b                               880b           900b

Cys Pro Arg Pro Gln Arg ... Thr Ser Thr Lys Arg Gln Ser Arg Arg Trp ... Ala Gln Val Asp Leu
Met Pro Ser Ala Ser Lys Met Asn Phe Asp Gln Lys Thr Lys Ser Pro Leu Val Ser Ala Gly ... Ser
Try Ala Leu Gly Leu Lys Asp Glu Leu Arg Pro Lys Asp Lys Val Ala Val Gly Lys Lys Arg Arg Leu Ile
```

```
GGGGCTGCGATGTrGGCGTTAGCA~TGrCTGTGCTGCTGCCTTCAAGGCGCGTCTCGGAGTCAATCATGGC
CCCCGACGCTACAACCGCAATCGTGACAGACGACGACGGAAGTTCGCGCAGAGCCTCAGTTAGTACCG
         920b                        940b                        960b         980b

Gly Leu Arg Cys Trp Arg ... His Cys Leu Cys Cys Leu Gln Ala Arg Leu Gly Val Asn His Gly
Gly Ala Ala Met Leu Ala Leu Ala Leu Ser Val Leu Leu Pro Ser Ser Ala Ser Alg Ser Gln Ser Trp
Trp Gly Cys Asp Val Gly Val Ser Thr Val Cys Ala Ala Ala Phe Lys Arg Val Ser Glu Ser Ile Met
```

```
AAACCACGCGTTAGGTTTCATCCAAGTTGGCATCAACATGGATGGGCCTGCAGTCGAGGATCTCTTCAAA
TTTGGTGCGCAATCCAAAGTAGGITCAACCGTAGTTGTACCTACCCGGACGTCAGCTCCTAGAGAAGTTT
                 1000b                    1020b                       1040b

Pro Arg Val Arg Phe His Pro Ser Trp His Gln His Gly Trp Ala Cys Ser Arg Gly Ser Leu Gln Arg
Thr Thr Arg ... Val Ser Ser Lys Leu Ala Ser Thr Trp Met Gly Leu Gln Ser Arg Ile Ser Ser Lys
Asn His Ala Leu Gly Phe Ile Gln Val Gly Ile Asn Met Asp Gly Ile Glu Asp Lys Leu Phe Lys
```

```
GAGGCTGGAAAAACCTAGGCACGACCGGTATTGTGTTGACTACTCCAAGTGGGATTCAACTCAGCGACCA
CTCCGACCTTTTGGATCCGTGCTGGCCATAACAACAACTGATGAGGTTCACCCTAAGTTGAGTCGGTGGT
                1060b                        1080b                  1100b         1120b

Gly Trp Lys Asn Leu Gly Thr Thr Gly Ile Val Leu Thr Thr Pro Ser Gly Ile Leu Ser His Gln
Arg Leu Glu Lys Pro Arg His Asp Arg Tyr Cys Val Asp Tyr Ser Lys Trp Asp Ser Thr Gln Pro Pro
Glu Ala Gly Lys Thr ... Ala Arg Pro Val Leu Cys ... Leu Leu Gln Val Gly Phe Asn Ser Ala Thr
```

FIG. 7D

AAAGTTACATCCCAATCAATTGACATACTCAGGCACTTCACTGACAAATCTCCAATTGTTGATTCGGCCT
TTTCAATGTAGGGTTAGTTAACTGTATGAGTCCGTGAAGTGACTGTTAGAGGTTAACAACTAAGCCCGGA
                                    1180b
                1160b

Lys Val Thr Ser Gln Ser Ile Asp Ile Leu Arg His Phe Thr Asp Lys Ser Pro Ile Val Asp Ser Ala
Lys Ser Tyr Ile Pro Ile Asn ... His Thr Gln Ala Leu His ... Gln Ile Ser Asn Cys ... Phe Gly
Lys Leu His Pro Asn Gln Leu Thr Tyr Ser Gly Thr Asn Leu Gln Leu Leu Ile Arg Pro

GTGCTACGCTCAAGTCAAACCCAGTTGGCATCTTCAATGGCGTGGCGTTTAAGGTTGCGGGTGGACTACC
CACGATGCGAGTTCAGTTGGGTCAACCGTAGAAGTTACCGCACCGCAAATTCCAACGCCACCTGATGG
                1220b                                  1260b
        1200b                                  1240b

Leu Arg Ser Ser Gln Thr Gln Leu Ala Ser Ser Met Ala Trp Arg Leu Arg Val Asp Tyr Arg
Ala Thr Leu Lys Ser Asn Pro Val Gly Ile Phe Asn Gly Val Ala Phe Lys Val Ala Gly Gly Leu Pro
Cys Tyr Ala Gln Val Lys Pro Ser Trp His Leu Gln Trp Arg Gly Val ... Gly Cys Gly Trp Thr Thr

GTCTGGTATGCCACTCACTTCCATCATCAACTCACTGAATCACTGTCTCATGGTAGGCTGTGCTGTCACT
CAGACCATACGGTGAGTGAGGTAGTAGTTGAGTGACTTAGTGACAGAGTACCATCCGACAGACAGTGA
                1280b                  130Gb                  1320b

Leu Val Cys His Ser Leu Pro Ser Ser Thr His ... Ile Thr Val Ser Trp ... Ala Val Leu Ser Leu
Ser Gly Met Pro Leu Thr Ser Ile Ile Asn Ser Leu Asn His Cys Leu Met Val Gly Cys Ala Val Thr
Val Trp Tyr Ala Thr His Phe His His Gln Leu Thr Glu Ser Leu His Gly Arg Leu Cys Cys His

AAGGCTCTCGAGGACTCAGGCGTGCAGGTGACTTGGAACATCTTCGACTCGATGGACCTGTTTACCTATG
TTCCGAGAGCTCCTGAGTCCGACGTCCCACGTCCACTGAACCTTGTAGAAGCTGAGCTACCTGGACAAATGGATAC
                1340b                  1360b          1380b                  1400b

Arg Leu Ser Arg Thr Gln Ala Cys Arg ... Leu Gly Thr Ser Ser Thr Arg Trp Thr Cys Leu Pro Met
Lys Ala Leu Glu Asp Ser Gly Val Gln Val Thr Trp Asn Ile Phe Asp Ser Met Asp Leu Phe Thr Tyr
... Gly Ser Arg Gly Leu Arg Arg Ala Gly Asp Leu His Leu Arg Asp Gly Pro Val Tyr Leu

FIG. 7E

GTGACGACGGTGTCTACATCGTCCCACCTCTCATCTCTTCTGTCATGCCCAAAGTCTTTGCGAACCTACG
CACTGCTGCCACAGATGTAGCAGGGTGAGAGTAGAGAAGACAGTACGGTTTCAGAAACGCTTGGATGC
                        1420b                                           1440b                                           1460b

Thr Thr.Val Ser.Thr Ser Ser His Leu Ser Ser Leu Leu Ser Cys Pro Lys Ser Leu Arg Thr Tyr Asp
Asp Asp Gly Val Tyr Ile Val Pro Pro Leu Ile Ser Ser Val Met Pro Lys Val Phe Ala Asn Leu Arg
... Arg Arg Cys Leu His Arg Pro Thr Ser His Leu Phe Cys His Ala Gln Ser Leu Cys Glu Pro Thr

ACAGTTCGGCCTGAAACCGACCCGGACCGATAAAAACGGATGCTGAGATAACGCCCATCCCTGCAGATGAA
TGTCAAGCCGGACTTTGGCTGGGCCTGGCCTATTTTGCCTACGACTCTATTGCGGGTAGGGACGTCTACTT
                        1480b                                           1500b                                           1520b                                           1540b

Ser Ser Ala ... Asn Arg Pro Gly Pro Ile Lys Arg Met Leu Arg ... Arg Pro Ser Leu Gln Met Asn
Gln Phe Gly Leu Lys Pro Thr Arg Thr Arg Phe Asp.Lys Thr Asp Ala Glu Ile Thr Pro Ile Pro Ala Asp Glu
Thr Val Arg Pro Glu Thr Arg Asp Pro Asp Arg ... Asn Gly Cys ... Asp Asn Ala His Pro Cys Arg ...

CCAGTTGAGTTTCTCAAACGAACACTTGTCCGAACTGAGAATGGCATACGAGCACTTCTGACAAATCCT
GGTCAACTCAAAGAGTTTGCTTGTGAACAGGCTTGACTCTTACCTATGCTCGTGAAGACCTGTTTAGGA
                        1560b                                           1580b                                           1600b

Gln Leu Ser Phe Ser Asn Glu His Leu Ser Glu Leu Arg Met Ala Tyr Glu His Phe Trp Thr Asn Pro
Pro Val Glu Phe Leu Lys Arg Thr Leu Val Arg Thr Glu Asn Gly Ile Arg Ala Leu Leu Asp Lys Ser
Thr Ser ... Val Ser Gln Thr Asn Thr Cys Pro Asn ... Glu Trp His Thr Ser Gly Gln Ile

CAATAATTCGGCAGTTCTACTACTACATCAAAGCAGAGAACACCGAGGAATGGACCAAACCGCCA
GTTATTAAGCCGTCAAGATGATGTAGTTTCGTCTCTTGTGGCTCCTTACCTGTTTGGCGGT
                        1620b                                           1640b                                           1660b

... Phe Gly Ser Ser Thr Thr Ser Lys Gln Arg Thr Pro Arg Asn Gly Pro Asn Arg
Ile Ile Arg Gln Phe Tyr Tyr Ile Lys Ala Glu Asn Thr Glu Glu Trp Thr Lys Pro Pro
Asn Asn Ser Ala Val Leu Leu His Gln Ser Arg Gly His Arg Gly Met Asp Gln Thr Ala

FIG. 7F

```
            GCTTCATGCAGAAACCAAAGCCAACAACCGTTGGTTCCATGTGATCGACACAGACAAAGC
         1 --------+---------+----------+----------+----------+-------+  60
            CGAAGTACGTCTTTGGTTTCGGTTGTTGGCAACCAAGGTACACTAGCTGTGTCTGTTTCG a         A  S  C  R  N  Q  S  Q  Q  P  L  V  P  C  D  R  H  R  Q  S  -
  b          L  H  A  E  T  K  A  N  N  R  W  F  H  V  I  D  T  D  K  A -
  c           F  M  Q  K  P  K  P  T  T  V  G  S  M  *                   -

CCTGGTGCCAGGCTTGCCTGATGGTTGGCCTGACACTACAATCCCAGAAAGTGTGACAGC
        61 --------+---------+----------+----------+----------+-------+  120
            GGACCACGGTCCGAACGGACTACCAACCGGACTGTGATGTTAGGGTCTTTCACACTGTCG a         P  G  A  R  L  A  *                                          -
  b          L  V  P  G  L  P  D  G  W  P  D  T  T  I  P  E  S  V  T  A -
  c           M  V  G  L  T  L  Q  S  Q  K  V  *                         -

AACCAATGGTGACTTCGCGTACGCGACCGATTTCTACAATCCGGCAACCAAAACTGTTGA
       121 --------+---------+----------+----------+----------+---------+ 180
            TTGGTTACCACTGAAGCGCATGCGCTGGCTAAAGATGTTAGGCCGTTGGTTTTGACAACT a                                                                      -
  b         T  N  G  D  F  A  Y  A  T  D  F  Y  N  P  A  T  K  T  V  D  -
  c          M  V  T  S  R  T  R  P  I  S  T  I  R  Q  P  K  L  L  T    -

CCCTACCAAGAACACCACGCCCTTCAAAGGCACATACATCTGTGGCACTTTATCAACGGT
       181 --------+---------+----------+----------+----------+---------+ 240
            GGGATGGTTCTTGTGGTGCGGGAAGTTTCCGTGTATGTAGACACCGTGAAATAGTTGCCA a                                                                      -
  b          P  T  K  N  T  T  P  F  K  G  T  Y  I  C  G  T  L  S  T  V -
  c           L  P  R  T  P  R  P  S  K  A  H  T  S  V  A  L  Y  Q  R  S -

CACCATACCCGAGGTTGACAATCAGAACTACGCAAAGAAGAAGCACAAAAGAAATCCCA
       241 --------+---------+----------+----------+----------+---------+ 300
            GTGGTATGGGCTCCAACTGTTAGTCTTGATGCGTTTCTTCTTCGTGTTTTCTTTAGGGT a                                                                      -
  b         T  I  P  E  V  D  N  Q  N  Y  A  K  ?  E  A  Q  K  K  S  Q  -
  c          P  Y  P  R  L  T  I  R  T  T  Q  R  ?  K  H  K  R  N  P  K -

AACAATGTACATAACAACTGCTGACATTGGGGATGGCAATGCCAGTCCACAACACAAAAT
       301 --------+---------+----------+----------+----------+---------+ 360
            TTGTTACATGTATTGTTGACGACTGTAACCCCTACCGTTACGGTCAGGTGTTGTGTTTTA a                                                                      -
  b         T  M  Y  I  T  T  A  D  I  G  D  G  N  A  S  P  Q  H  K  I  -
  c          Q  C  T  *                             M  A  M  P  V  H  N  T  K  F -
```

FIG. 8A

```
           TTCACCTCAGAGATTGATTGTCTTCTTCGACGGTCCGGAGAGCACGATGGACATCAACGT
       361 ---------+---------+----------+----------+----------+--------+ 420
           AAGTGGAGTCTCTAACTAACAGAAGAAGCTGCCAGGCCTCTCGTGCTACCTGTAGTTGCA
a                                                                        -
b            S  P  Q  R  L  I  V  F  F  D  G  P  E  S  T  M  D  I  N  V  -
c              H  L  R  D  *

CACGTTGAGTCCGCTTGGGTTCACACTTGTGGACGGTCAACCAATTGGCTCCAGTTCCAG
       421 ---------+---------+----------+----------+----------+--------+ 480
           GTGCAACTCAGGCGAACCCAAGTGTGAACACCTGCCAGTTGGTTAACCGAGGTCAAGGTC
a                                                                        -
b            T  L  S  P  L  G  F  T  L  V  D  G  Q  P  I  G  S  S  S  S
c

CAAAGTTGTCaGGAtTGCTACACTCCCAGAAGCCATTACACAAGGAGGGAACTACCCAAT
       481 ---------+---------+----------+----------+----------+--------+ 540
           GTTTCAACAGtCCTaACGATGTGAGGGTCTTCGGTAATGTGTTCCTCCCTTGATGGGTTA
a                                                                        -
b            K  V  V  R  I  A  T  L  P  E  A  I  T  Q  G  G  N  Y  P  I  -
c

CTTCTATGTGAACAAAgTCaAGATTGGATACTTTGACAGGCAAACCACAGAgTGTTACaA
       541 ---------+---------+----------+----------+----------+--------+ 600
           GAAGATACACTTGTTTcAGtTCTAACCTATGAAACTGTCCGTTTGGTGTCTcACAATGtT
a                                                                        -
b            F  Y  V  N  K  V  K  I  G  Y  F  D  R  Q  T  T  E  C  Y  N  -
c               M  *

CAGCCAAGTTCTGATGACaTCgCagAAACTTGCCGAgGGAAATTACaAcCTcCCCCCTGA
       601 ---------+---------+----------+----------+----------+--------+ 660
           GTCGGTTCAAGACTACTGtAGcGtcTTTGAACGGCTcCCTTTAATGtTgGAgGGGGGACT
a                                                                        -
b            S  Q  V  L  M  T  S  Q  K  L  A  E  G  N  Y  N  L  P  P  D  -
c

CTcCCTTGCCGTGTACAGAATCaCAgAcTCTTCTTCTCAATGGTTCgACATCGGGATCAA
       661 ---------+---------+----------+----------+----------+--------+ 720
           GAgGGAACGGCACATGTCTTAGtGTcTgAGAAGAAGAGTTACCAAGcTGTAGCCCTAGTT
A                                                        M  V  R  H  R  D  Q -
b            S  L  A  V  Y  R  I  T  D  S  S  S  Q  W  F  D  I  G  I  N  -
c

CCATGATGGtTTCTCgTTTGTTGGGCTGTCTGAcCTTCCCTCTGATCTAgAAtTTCC
       721 ---------+---------+----------+----------+----------+-----+ 778
           GGTACTACCaAAGAGcAAACAACCCGACAGACTgGAAGGGAGACTAGATCTTaAAGG
a            P  *                                                         -
b            H  D  G  F  S  F  V  G  L  S  D  L  P  S  D  L  E  F  P   -
c            M  M  V  S  R  L  L  G  C  L  T  F  P  L  I  *
```

FIG. 8B

```
       CCtCaCTTCgAcCTTCaTGGGAgTgCagCTAgCACgTgTCaAgCTAgCaTCaAAGGTCaA
   781 --------+---------+----------+----------+----------+--------+ 840
       GGaGtGAAGcTgGAAGtACCCTcAcGtcGATcGTGcAcAGtTcGATcGtAGtTTCCAGtT
a
b       L  T  S  T  F  M  G  V  Q  L  A  R  V  K  L  A  S  K  V  K  -
c

AAgCaCagCCagAACaATaTGAACTaTgCaAATTTGGGCatTgATCTCTTCaACagCaTT
   841 --------+---------+----------+----------+----------+--------+ 900
       TTcGtGtcGGtcTTGtTAtACTTGAtAcGtTTAAACCCGtaAcTAGAGAAGtTGtcGtAA
a                     M  N  Y  A  N  L  G  I  D  L  F  N  S  I   -
b       S  T  A  R  T  I  *   M  Q  I  W  A  L  I  S  S  T  A  L  -
c gcGAATgCtGCTGTTgAgGGGAAgAAACTagATTTGGCCtCAAAgAgtTTTCagTTgAAg
   901 --------+---------+----------+----------+----------+--------+ 960
       cgGTTAcGaCGACAACTcCCCTTcTTTgAtcTAAACCGGaGTTTcTcaAAAGtcAAcTTc
a       A  N  A  A  V  E  G  K  K  L  D  L  A  S  K  S  F  Q  L  K  -
b        P  M  L  L  L  R  G  R  N  *
c

TcCgtgcaCtGGAcACagAAAGGGAcTtCaaCTacgCCaggCTCGCATTTGAAAAACACn
   961 --------+---------+----------+----------+----------+--------+ 1020
       AgGcacgtGaCCTgTGtcTTTCCCTgAaGttGAtgcGGtccGAGCGTAAACTTTTTGTGn
a       S  V  H  W  T  Q  K  G  T  S  T  T  P  G  S  H  L  K  N  T  -
b
c AATTTAACACnAATAACGAACTAAGAATCTATGGTGATGCGTTACGCCTTCAAGCGCTTC
  1021 --------+---------+----------+----------+----------+--------+ 1080
       TTAAATTGTGnTTATTGCTTGATTCTTAGATACCACTACGCAATGCGGAAGTTCGCGAAG
a       N  L  T  ?  I  T  N  *   M  V  M  R  Y  A  F  K  R  F  -
b
c GCGCTTCTGGACTACGCATCAATCCATACTCmAATGGtCGcCAAATTTACCAAgAtGAAg
  1081 --------+---------+----------+----------+----------+--------+ 1140
       CGCGAAGACCTGATGCGTAGTTAGGTATGAGkTTACCaGCgGTTTAAATGGTTcTaCTTc
a       A  L  L  D  Y  A  S  I  H  T  ?  M  V  A  K  F  T  K  M  K  -
b
c CTGAcCTTGCAAATCTGCaCTCTTATTATAgCTTCTATAAAACGGACTAgTTCCaAcCTG
  1141 --------+---------+----------+----------+----------+--------+ 1200
       GACTgGAACGTTTAGACGtGAGAATAATATcGAAGATATTTTGCCTgATcAAGGtTgGAC
a       L  T  L  Q  I  C  T  L  I  I  A  S  I  K  R  T  S  S  N  L  -
b
c
```

FIG. 8C

```
        CTTAACAAtTTTCTACgActTTAgCCTATGCTTTaTTTCCTCTTATCAGTTCCTTATTTT
   1201 --------+---------+----------+-----------+----------+--------+ 1260
        GAATTGTTaAAAGATGcTgaAATcGGATACGAAAtAAAGGAGAATAGTCAAGGAATAAAA
  a     L   N   N   F   L   R   L   *       M   L   Y   F   L   L   S   V   P   Y   F    -
  b                                                                                       -
  c                                                                                       -

GTTAGTTAAGTGTTTTATATTTTCACCTCTGTCTAATTATTTAATCAATGGGATAATTGT
   1261 --------+---------+----------+-----------+----------+--------+ 1320
        CAATCAATTCACAAAATATAAAAGTGGAGACAGATTAATAAATTAGTTACCCTATTAACA
  a     V   S   *                                                                         -
  b                                                                                       -
  c                                                                       M   G   *       -

TCTTAATCTAGTAGACTGTAGACTTAGCCAATTGGTAGGTTGCATTAGGA
   1321 --------+---------+----------+-----------+---------+ 1370
        AGAATTAGATCATCTGACATCTGAATCGGTTAACCATCCAACGTAATCCT
```

FIG. 8D

|        |   |   |   |   |   |   |   |   |   |   |   |   |   |   |   |   |   |   |   |   |   |   |   |   |
|--------|---|---|---|---|---|---|---|---|---|---|---|---|---|---|---|---|---|---|---|---|---|---|---|---|
| SMSV-5 | P | G | D | C | G | L | P | Y | T | D | E | H | G | – | – | – | – | V | V | V | G | L | H | A | G |
| FCV    | P | G | D | C | G | L | P | Y | I | D | D | N | G | – | – | – | – | R | V | T | G | L | H | T | G |
| RHDV   | H | G | D | C | G | L | P | L | Y | D | S | S | G | – | – | – | – | K | I | V | A | I | H | T | G |
| SV     | P | G | D | C | G | A | P | Y | V | Y | K | R | A | N | D | W | – | V | C | G | V | H | A | A |

FIG. 10

RNA Polymerase Region

```
SMSV-6  RYCVDYSKWDSTQPPKVTSQSIDILRHFTDK-SPIVDSACATLKSNPVGIFNGVAFK
FCV     VFAVDYSKWDSTQSPRVSAASIDILRYFSDR-TPIVDSATNTLKSPPLAVFNGVAVK
RHDV    FLCLDYSKWDSTMSPCVVRLAIDILADCCEQ-TELTKSVVLTLKSHPMTILDAMIVQ
SV      HFDADYTAWDSTQNRQIMTESFSIMCR---LTASPELASVVAQDLLAPSEMDVGDYVI

SMSV-6  VAG-GLPSGMPLTSIINSLNHCLMVGCAVTKALEDSGVQVTWNIFDSMDLFTYGDDG
FCV     VSS-GLPSGMPLTSVINSLNHCLYVGCAILQSLEARNVPVTWNLFSTFDMMTYGDDG
RHDV    TKR-GLPSGMPETSVINSICHWLLWSAAVYKSCAEIGLHCS-NLYEDAPFYTYGDDG
SV      RVKEGLPSGFPCTSQVNSINHWLITLCALSEVTGLSPD-V---IQSMSYFSFYGDDE

SMSV-6  VYIVPPLIS-SVMPKVFAN
FCV     VY-MFPTMYASISDQIFAN
RHDV    VYAMTPMMV-SLLPAIIEN
SV      IVSTDIEFDPAKLTQVLRE
```

FIG. 11

Monoclonal antibodies used to identify neutralizing epitopes for vaccines. Partially cross-neutralizing monoclonal antibodies from hybridoma supernatants as listed below.

| Calicivirus | Mab | | | |
|---|---|---|---|---|
| SMSV-5 | AWS-5 | Plate 2 | Well | B 6 |
| SMSV-12 | AWS-5 | Plate 2 | Well | B 7 |
| F-9 | AWS-5 | Plate 8 | Well | A 11 |
| SMSV-8 | AWS-6 | Plate 5A | Well | 1B |
| | AWS-6 | Plate 1A | Wells | 4C, 1H |
| | AWS-6 | Plate 2A | Wells | 5E, 7 G |
| | AWS-6 | Plate 3A | Wells | A 5, G 1 |
| | AWS-6 | Plate 4A | Wells | A 7, H8 |
| | AWS-5 | Plate 1 | Well | B 12 |
| | AWS-5 | Plate 3 | Well | B 12 |
| | AWS-5 | Plate 4 | Wells | A2, A12 |

FIG. 12

Monoclonal antibodies that are reactive against all or nearly all known variants of the vesicular genus.

4 AD8D8*

2 AF11B11       FITC labeled and conditioned media.

2 A$^1$C5H12

*Used for identifying VMK cells infected with 38 stereotypes of caliciviruses (@ 1:100 dilution) by FAB 5/98.

FIG. 13

Polyclonal antibodies and test serum reactivitiy to caliciviruses.

| Serum | Calicivirus Antigen Pools | | | | | |
|---|---|---|---|---|---|---|
| | A | B | C | D | E | F |
| Rabbit Prebleed 7420 | - | - | - | - | - | - |
| Rabbit Prebleed SMSV-15 | - | - | - | - | - | - |
| Porcine Infected Pig 7420 | - | - | - | - | + | + |
| Rabbit Primate 022 | ++ | ++ | ++ | ++ | ++ | ++ |
| Rabbit F-9 | +++ | +++ | +++ | +++ | +++ | +++ |
| Rabbit 7420 | +/- | + | + | + | + | + |
| Rabbit Reptile | +++ | +++ | +++ | +++ | +++ | +++ |
| Rabbit SMSV-1 | +++ | +++ | +++ | +++ | +++ | +++ |
| Rabbit SMSV-2 | +++ | +++ | +++ | +++ | +++ | +++ |
| Rabbit SMSV-3 | +++ | +++ | +++ | +++ | +++ | +++ |
| Rabbit SMSV-4 | +++ | +++ | +++ | +++ | +++ | +++ |
| Rabbit SMSV-5 | +++ | +++ | +++ | +++ | +++ | +++ |
| Rabbit SMSV-6 | +++ | +++ | +++ | +++ | +++ | +++ |
| Rabbit SMSV-7 | +++ | +++ | +++ | +++ | +++ | +++ |
| Rabbit SMSV-8 | +/- | +++ | + | ++ | + | ++ |
| Rabbit SMSV-9 | +++ | +++ | +++ | +++ | +++ | +++ |
| Rabbit SMSV-10 | +++ | +++ | +++ | +++ | +++ | +++ |
| Rabbit SMSV-11 | +++ | +++ | +++ | +++ | +++ | +++ |
| Rabbit SMSV-12 | +/- | + | + | ++ | + | ++ |
| Rabbit SMSV-13 | +++ | +++ | +++ | +++ | +++ | +++ |
| Rabbit SMSV-14 | +++ | +++ | +++ | +++ | +++ | +++ |
| Rabbit SMSV-15 | +++ | +++ | +++ | +++ | +++ | +++ |
| Rabbit VESV-A | +++ | +++ | +++ | +++ | +++ | +++ |
| Rabbit VESV-B | +++ | +++ | +++ | +++ | +++ | +++ |
| Rabbit VESV-C | + | ++ | ++ | ++ | ++ | ++ |
| Rabbit VESV-D | +++ | +++ | +++ | +++ | +++ | +++ |
| Rabbit VESV-E | +++ | +++ | +++ | +++ | +++ | +++ |
| Rabbit VESV-F | +++ | +++ | +++ | +++ | ++ | +++ |
| Rabbit VESV-G | +++ | +++ | +++ | +++ | +++ | +++ |
| Rabbit VESV-H | +++ | +++ | +++ | +++ | +++ | +++ |
| Rabbit VESV-I | +++ | +++ | +++ | +++ | +++ | +++ |
| Rabbit VESV-J | ++ | ++ | ++ | ++ | ++ | +++ |
| Rabbit VESV-K | +++ | +++ | +++ | +++ | +++ | +++ |
| Human HCV (UK-3) | +/- | + | + | + | ++ | + |
| Human HCV McSwiggan | +++ | +++ | +++ | +++ | +++ | +++ |
| Human UK-1 HCV | +++ | +++ | +++ | +++ | +++ | +++ |
| Human UK-2 HCV | - | +/- | + | + | +/- | + |
| Human HCV Richardson | + | ++ | ++ | +++ | ++ | +++ |
| | SMSV-1<br>SMSV-2<br>SMSV-4<br>SMSV-5 | SMSV-6<br>SMSV-7<br>SMSV-8<br>SMSV-9 | SMSV-10<br>SMSV-11<br>SMSV-12<br>SMSV-13 | SMSV-14<br>SMSV-15<br>W-6<br>MV20-3 | TMK<br>F-9<br>7420<br>Reptile | Gp. A<br>Gp. B<br>Gp. C<br>Gp. D<br>Gp. E |

FIG. 14

SEQUENCE LISTING

```
<160> NUMBER OF SEQ ID NOS: 14

<210> SEQ ID NO 1
<211> LENGTH: 453
<212> TYPE: DNA
<213> ORGANISM: Caliciviridae
<220> FEATURE:
<221> NAME/KEY: CDS
<222> LOCATION: (3)..(452)

<400> SEQUENCE: 1 tg gat ggg cct gca gtc gag gat ctc ttc aaa agg ctg gaa aaa cct        47
   Asp Gly Pro Ala Val Glu Asp Leu Phe Lys Arg Leu Glu Lys Pro
    1               5                  10                  15 agg cac gac cgg tat tgt gtt gac tac tcc aag tgg gat tca act cag       95
Arg His Asp Arg Tyr Cys Val Asp Tyr Ser Lys Trp Asp Ser Thr Gln
                20                  25                  30 cca cca aaa gtt aca tcc caa tca att ggc ata ctc agg cac ttc act      143
Pro Pro Lys Val Thr Ser Gln Ser Ile Gly Ile Leu Arg His Phe Thr
            35                  40                  45 gac aaa tct cca att gtt gat tcg gcc tgt gct aca ctc aag tca agc      191
Asp Lys Ser Pro Ile Val Asp Ser Ala Cys Ala Thr Leu Lys Ser Ser
        50                  55                  60 cca gtt ggc atc ttc aat ggc gtg gcg ttt aag gtt gcg ggt gga cca      239
Pro Val Gly Ile Phe Asn Gly Val Ala Phe Lys Val Ala Gly Gly Pro
    65                  70                  75 ccg tct ggt atg cca ctc act tcc atc atc aac tca ctg aat cac tgt      287
Pro Ser Gly Met Pro Leu Thr Ser Ile Ile Asn Ser Leu Asn His Cys
80                  85                  90                  95 ctc atg gta ggc tgt gct gtc act aag gct ctc gag gac tca ggc gtg      335
Leu Met Val Gly Cys Ala Val Thr Lys Ala Leu Glu Asp Ser Gly Val
                100                 105                 110 cag gtg act tgg aac atc ttc gac tcg atg gac ctg ttt acc tat ggt      383
Gln Val Thr Trp Asn Ile Phe Asp Ser Met Asp Leu Phe Thr Tyr Gly
            115                 120                 125 gac gac ggt gtc tac atc gtc cca cct ctc atc tct tct gtc atg ccc      431
Asp Asp Gly Val Tyr Ile Val Pro Pro Leu Ile Ser Ser Val Met Pro
        130                 135                 140 aaa gtc ttt gcg aac ctg aaa c                                        453
Lys Val Phe Ala Asn Leu Lys
    145                 150

<210> SEQ ID NO 2
<211> LENGTH: 150
<212> TYPE: PRT
<213> ORGANISM: Caliciviridae

<400> SEQUENCE: 2

Asp Gly Pro Ala Val Glu Asp Leu Phe Lys Arg Leu Glu Lys Pro Arg
  1               5                  10                  15

His Asp Arg Tyr Cys Val Asp Tyr Ser Lys Trp Asp Ser Thr Gln Pro
             20                  25                  30
```

```
Pro Lys Val Thr Ser Gln Ser Ile Gly Ile Leu Arg His Phe Thr Asp
         35                  40                  45
Lys Ser Pro Ile Val Asp Ser Ala Cys Ala Thr Leu Lys Ser Ser Pro
     50                  55                  60
Val Gly Ile Phe Asn Gly Val Ala Phe Lys Val Ala Gly Gly Pro Pro
 65                  70                  75                  80
Ser Gly Met Pro Leu Thr Ser Ile Ile Asn Ser Leu Asn His Cys Leu
                 85                  90                  95
Met Val Gly Cys Ala Val Thr Lys Ala Leu Glu Asp Ser Gly Val Gln
                100                 105                 110
Val Thr Trp Asn Ile Phe Asp Ser Met Asp Leu Phe Thr Tyr Gly Asp
            115                 120                 125
Asp Gly Val Tyr Ile Val Pro Pro Leu Ile Ser Ser Val Met Pro Lys
        130                 135                 140
Val Phe Ala Asn Leu Lys
145                 150
```

<210> SEQ ID NO 3
<211> LENGTH: 1672
<212> TYPE: DNA
<213> ORGANISM: Caliciviridae

<400> SEQUENCE: 3

```
aaaagattta aagataaatg gtgaattggc tactttcagg ctgaacagca ccctcccaac    60
tgctgttcca gtcggaacat ccaaacccat taaggaccca tggggaaacc cagtgtccac   120
agattggcaa ttcaaagaat ttaacaccac atctggacac atctatggtg cttcagcatc   180
atcctgttcc ttaacccgcc aggtgattgt gggctaccat acaccgacga cacggtgtt   240
gtggtgggcc tgcatgcggg atcgggtggt gacaagtgcc cctcgcgtaa actcgtcgta   300
ccttacgtta aggtcgacat gaagattcgc gacacgtgca caaggagta ctacaaggac   360
aatcaaccaa tcatttctta caaggactg ctggtaaagg aaacagggga tccaagaact   420
atcatgaagg gaacgcgact ccacgtatca cccgctcaca cgggtgacta cgaggagtgc   480
tcccatcaac cagcctcttt gggtgcaggg gatccaagat gtcccatttc cctcaccggg   540
atcatggtaa caacctgca accatacaca gaggcagctc ctggaccaga caccagcaca   600
ctcaaccgag tgtcgaaaat gctgactacc cacatggaag gctacgtgcc caaagtccac   660
aaaactgagg aagacatgct ttcggcattc tacatgctga atcatgacac atcctgcggc   720
ccttacatcg gcggccggaa aaagaccat gttaaggacg gtgtcctaga taaggccttg   780
ctggacctcc tcagttcaaa atggaaccgt gctaaactgg gcttagctct accacacgag   840
tatgccctcg gcctcaaaga tgaacttcga ccaaaagaca agtcgccgt tggtaagcgc   900
aggttgatct ggggctgcga tgttggcgtt agcactgtct gtgctgctgc cttcaagcgc   960
gtctcggagt caatcatggc aaaccacgcg ttaggtttca tccaagttgg catcaacatg  1020
gatgggcctg cagtcgagga tctcttcaaa gaggctggaa aaacctaggc acgaccggta  1080
ttgtgttgac tactccaagt gggattcaac tcagccacca aaagttacat cccaatcaat  1140
tgacatactc aggcacttca ctgacaaatc tccaattgtt gattcggcct gtgctacgct  1200
caagtcaaac ccagttggca tcttcaatgg cgtggcgttt aaggttgcgg gtggactacc  1260
gtctggtatg ccactcactt ccatcatcaa ctcactgaat cactgtctca tggtaggctg  1320
tgctgtcact aaggctctcg aggactcagg cgtgcaggtg acttggaaca tcttcgactc  1380
gatggacctg tttacctatg gtgacgacgg tgtctacatc gtcccacctc tcatctcttc  1440
```

-continued

```
tgtcatgccc aaagtctttg cgaacctacg acagttcggc ctgaaaccga cccggaccga   1500
taaaacggat gctgagataa cgcccatccc tgcagatgaa ccagttgagt ttctcaaacg   1560
aacacttgtc cgaactgaga atggcatacg agcacttctg acaaatcct caataattcg    1620 gcagttctac tacatcaaag cagagaacac cgaggaatgg accaaaccgc ca           1672
```

<210> SEQ ID NO 4
<211> LENGTH: 882
<212> TYPE: DNA
<213> ORGANISM: Caliciviridae

<400> SEQUENCE: 4

```
cttcatgcag aaaccaaagc caacaaccgt tggttccatg tgatcgacac agacaaagcc    60
ctggtgccag gcttgcctga tggttggcct gacactacaa tcccagaaag tgtgacagca   120
accaatggtg acttcgcgta cgcgaccgat ttctacaatc cggcaaccaa aactgttgac   180
cctaccaaga caccacgcc cttcaaggca catacatct gtggcacttt atcaacggtc    240
accatacccg aggttgacaa tcagaactac gcaaagaagg aagcacaaaa gaaatcccaa   300
acaatgtaca taacaactgc tgacattggg gatggcaatg ccagtccaca acacaaaatt   360
tcacctcaga gattgattgt cttcttcgac ggtccggaga gcacgatgga catcaacgtc   420
acgttgagtc cgcttgggtt cacacttgtg gacggtcaac caattggctc cagttccagc   480
aaagttgtca ggattgctac actcccagaa gccattacac aaggagggaa ctacccaatc   540
ttctatgtga acaaagtcaa gattggatac tttgacaggc aaaccacaga gtgttacaac   600
agccaagttc tgatgacatc gcagaaactt gccgagggaa attacaacct ccccctgac    660 tcccttgccg tgtacagaat cacagactct tcttctcaat ggttcgacat cgggatcaac   720
catgatggtt tctcgtttgt tgggctgtct gaccttccct ctgatctaga atttcccctc   780
acttcgacct tcatgggagt gcagctagca cgtgtcaagc tagcatcaaa ggtcaaaagc   840
acagccagaa caatagacta caaggacgac gatgacaagt aa                     882
```

<210> SEQ ID NO 5
<211> LENGTH: 293
<212> TYPE: PRT
<213> ORGANISM: Caliciviridae

<400> SEQUENCE: 5

```
Leu His Ala Glu Thr Lys Ala Asn Asn Arg Trp Phe His Val Ile Asp
  1               5                  10                  15

Thr Asp Lys Ala Leu Val Pro Gly Leu Pro Asp Gly Trp Pro Asp Thr
             20                  25                  30

Thr Ile Pro Glu Ser Val Thr Ala Thr Asn Gly Asp Phe Ala Tyr Ala
         35                  40                  45

Thr Asp Phe Tyr Asn Pro Ala Thr Lys Thr Val Asp Pro Thr Lys Asn
     50                  55                  60

Thr Thr Pro Phe Lys Gly Thr Tyr Ile Cys Gly Thr Leu Ser Thr Val
 65                  70                  75                  80

Thr Ile Pro Glu Val Asp Asn Gln Asn Tyr Ala Lys Lys Glu Ala Gln
                 85                  90                  95

Lys Lys Ser Gln Thr Met Tyr Ile Thr Thr Ala Asp Ile Gly Asp Gly
            100                 105                 110

Asn Ala Ser Pro Gln His Lys Ile Ser Pro Gln Arg Leu Ile Val Phe
        115                 120                 125
```

```
Phe Asp Gly Pro Glu Ser Thr Met Asp Ile Asn Val Thr Leu Ser Pro
    130                 135                 140
Leu Gly Phe Thr Leu Val Asp Gly Gln Pro Ile Gly Ser Ser Ser Ser
145                 150                 155                 160
Lys Val Val Arg Ile Ala Thr Leu Pro Glu Ala Ile Thr Gln Gly Gly
                165                 170                 175
Asn Tyr Pro Ile Phe Tyr Val Asn Lys Val Lys Ile Gly Tyr Phe Asp
            180                 185                 190
Arg Gln Thr Thr Glu Cys Tyr Asn Ser Gln Val Leu Met Thr Ser Gln
        195                 200                 205
Lys Leu Ala Glu Gly Asn Tyr Asn Leu Pro Pro Asp Ser Leu Ala Val
    210                 215                 220
Tyr Arg Ile Thr Asp Ser Ser Gln Trp Phe Asp Ile Gly Ile Asn
225                 230                 235                 240
His Asp Gly Phe Ser Phe Val Gly Leu Ser Asp Leu Pro Ser Asp Leu
                245                 250                 255
Glu Phe Pro Leu Thr Ser Thr Phe Met Gly Val Gln Leu Ala Arg Val
            260                 265                 270
Lys Leu Ala Ser Lys Val Lys Ser Thr Ala Arg Thr Ile Asp Tyr Lys
        275                 280                 285
Asp Asp Asp Asp Lys
    290

<210> SEQ ID NO 6
<211> LENGTH: 29
<212> TYPE: DNA
<213> ORGANISM: Caliciviridae
<220> FEATURE:
<223> OTHER INFORMATION: Description of Artificial Sequence: PCR Primer

<400> SEQUENCE: 6
gtggtcggcc ggggctcgtt ggggaggtg                                    29

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: PCR Primer

<400> SEQUENCE: 7
cgggtcggtt tcagaccaaa c                                            21

<210> SEQ ID NO 8
<211> LENGTH: 18
<212> TYPE: DNA
<213> ORGANISM: Artificial Sequence
<220> FEATURE:
<223> OTHER INFORMATION: Description of Artificial Sequence: PCR Primer

<400> SEQUENCE: 8
atccaagttg gcatcaaa                                                18

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: PCR Primer

<400> SEQUENCE: 9
```

```
cgggtcggtt tcagaccaaa c                                              21
```

<210> SEQ ID NO 10
<211> LENGTH: 18
<212> TYPE: DNA
<213> ORGANISM: Artificial Sequence
<220> FEATURE:
<223> OTHER INFORMATION: Description of Artificial Sequence: PCR Primer

<400> SEQUENCE: 10

```
atccaagttg gcatcaaa                                                  18
```

<210> SEQ ID NO 11
<211> LENGTH: 512
<212> TYPE: PRT
<213> ORGANISM: Caliciviridae

<400> SEQUENCE: 11

```
Lys Ile Arg Met Val Asn Trp Leu Leu Ser Gly Thr Ala Pro Ser Gln
  1               5                  10                  15

Leu Leu Phe Gln Ser Glu His Pro Asn Pro Leu Arg Thr His Gly Glu
             20                  25                  30

Thr Gln Cys Pro Gln Gly Asn Ser Lys Asn Thr Pro His Leu Asp Thr
         35                  40                  45

Ser Met Val Leu Gln His His Pro Val Pro Pro Ala Arg Leu Trp Ala
     50                  55                  60

Thr His Arg Arg Thr Arg Cys Cys Gly Gly Pro Ala Cys Gly Gly Trp
 65                  70                  75                  80

Gln Val Pro Leu Ala Thr Arg Thr Leu Arg Gly Arg His Glu Asp
                 85                  90                  95

Ser Arg His Val His Lys Gly Val Gln Gly Gln Ser Thr Asn His Phe
            100                 105                 110

Leu Gln Arg Thr Ala Gly Lys Gly Asn Arg Gly Ser Lys Asn Tyr His
        115                 120                 125

Glu Gly Asn Ala Thr Pro Arg Thr Arg Ser His Gly Leu Arg Gly Val
    130                 135                 140

Leu Pro Ser Thr Ser Leu Phe Gly Cys Arg Gly Ser Lys Met Ser His
145                 150                 155                 160

Phe Pro His Arg Asp His Gly Lys Gln Pro Ala His Arg Gly Ser Ser
                165                 170                 175

Trp Thr Arg His Gln His Thr Gln Pro Ser Val Glu Asn Ala Asp Tyr
            180                 185                 190

Pro His Gly Arg Leu Arg Ala Gln Ser Pro Gln Asn Gly Arg His Ala
        195                 200                 205

Phe Gly Leu His Ala Glu Ser His Leu Arg Pro Leu His Arg Arg Pro
    210                 215                 220

Glu Lys Arg Pro Cys Gly Arg Cys Pro Arg Gly Leu Ala Gly Pro Pro
225                 230                 235                 240

Gln Phe Lys Met Glu Pro Cys Thr Gly Leu Ser Ser Thr Thr Arg Val
                245                 250                 255

Cys Pro Arg Pro Gln Arg Thr Ser Thr Lys Arg Gln Ser Arg Arg Trp
            260                 265                 270

Ala Gln Val Asp Leu Gly Leu Arg Cys Trp Arg His Cys Leu Cys Cys
        275                 280                 285

Cys Leu Gln Ala Arg Leu Gly Val Asn His Gly Pro Arg Val Arg Phe
    290                 295                 300
```

```
His Pro Ser Trp His Gln His Gly Trp Ala Cys Ser Arg Gly Ser Leu
305                 310                 315                 320

Gln Arg Gly Trp Lys Asn Leu Gly Thr Gly Val Leu Thr Thr Pro
                325                 330                 335

Ser Gly Gln Leu Ser His Gln Lys Leu His Pro Asn Gln Leu Thr Tyr
                340                 345                 350

Ser Gly Thr Ser Leu Thr Asn Leu Gln Leu Leu Arg Pro Leu Arg Ser
                355                 360                 365

Ser Gln Thr Gln Leu Ala Ser Ser Met Ala Trp Arg Leu Arg Leu Arg
                370                 375                 380

Asp Tyr Arg Leu Cys His Ser Leu Pro Ser Ser Thr His Ile Thr Val
385                 390                 395                 400

Ser Trp Ala Val Leu Ser Leu Arg Leu Ser Arg Thr Gln Ala Cys Arg
                405                 410                 415

Leu Gly Thr Ser Ser Thr Arg Trp Thr Cys Leu Pro Met Thr Thr Val
                420                 425                 430

Ser Thr Ser Ser His Leu Ser Ser Leu Leu Ser Cys Pro Lys Ser Leu
                435                 440                 445

Arg Thr Tyr Asp Ser Ala Asn Arg Pro Gly Pro Lys Arg Met Leu Arg
                450                 455                 460

Arg Pro Ser Leu Gln Met Asn Gln Leu Ser Phe Ser Asn Glu His Leu
465                 470                 475                 480

Ser Glu Leu Arg Met Ala Tyr Glu His Phe Trp Thr Asn Pro Phe Gly
                485                 490                 495

Ser Ser Thr Thr Ser Lys Gln Arg Thr Pro Arg Asn Gly Pro Asn Arg
                500                 505                 510

<210> SEQ ID NO 12
<211> LENGTH: 512
<212> TYPE: PRT
<213> ORGANISM: Caliciviridae

<400> SEQUENCE: 12

Lys Asp Leu Lys Asn Gly Glu Leu Ala Thr Phe Arg Leu Asn Ser Thr
1               5                   10                  15

Leu Pro Thr Ala Val Pro Val Gly Thr Ser Lys Pro Lys Asp Pro Trp
                20                  25                  30

Gly Asn Pro Val Ser Thr Asp Trp Gln Phe Lys Glu Asn Thr Thr Ser
                35                  40                  45

Gly His Tyr Gly Ala Ser Ala Ser Cys Ser Leu Thr Arg Gln Val
        50                  55                  60

Val Gly Tyr His Thr Pro Thr Asn Thr Val Leu Trp Trp Cys Met Arg
65                  70                  75                  80

Asp Arg Val Val Thr Ser Ala Arg Val Asn Ser Ser Tyr Leu Thr Leu
                85                  90                  95

Arg Ser Thr Arg Phe Ala Thr Arg Ala Gln Arg Ser Thr Arg Thr Asn
                100                 105                 110

Gln Ser Phe Leu Thr Lys Asp Cys Trp Arg Lys Gln Gly Gln Glu Leu
                115                 120                 125

Ser Arg Glu Arg Asp Ser Thr Tyr His Pro Leu Thr Arg Val Thr Thr
                130                 135                 140

Arg Ser Pro Ile Asn Gln Pro Leu Trp Val Gln Gly Gln Asp Val Pro
145                 150                 155                 160

Phe Pro Ser Pro Gly Ser Trp Thr Thr Cys His Thr Gln Arg Gln Leu
                165                 170                 175
```

-continued

```
Leu Asp Gln Thr Pro Ala His Ser Thr Glu Cys Arg Lys Cys Leu Pro
            180                 185                 190

Thr Trp Lys Ala Thr Cys Pro Lys Ser Thr Lys Leu Arg Lys Thr Cys
        195                 200                 205

Phe Arg His Ser Thr Cys Met Thr His Pro Ala Ala Leu Thr Ser Ala
    210                 215                 220

Ala Gly Lys Lys Thr Met Leu Arg Thr Val Ser Arg Pro Cys Trp Thr
225                 230                 235                 240

Ser Ser Val Gln Asn Gly Thr Val Leu Asn Trp Ala Leu Tyr His Thr
                245                 250                 255

Ser Met Pro Ser Ala Ser Lys Met Asn Phe Asp Gln Lys Thr Lys Ser
            260                 265                 270

Pro Leu Val Ser Ala Gly Ser Gly Ala Ala Met Leu Ala Leu Ala Leu
        275                 280                 285

Ser Val Leu Leu Pro Ser Ser Ala Ser Arg Ser Gln Ser Trp Thr Thr
    290                 295                 300

Arg Val Ser Ser Lys Leu Ala Ser Thr Trp Met Gly Leu Gln Ser Arg
305                 310                 315                 320

Ser Ser Lys Arg Leu Glu Lys Pro Arg His Asp Arg Tyr Cys Val Asp
                325                 330                 335

Tyr Ser Lys Trp Asp Ser Thr Gln Pro Pro Lys Val Thr Ser Gln Ser
            340                 345                 350

Asp Leu Arg His Phe Thr Asp Lys Ser Pro Val Asp Ser Ala Ala Thr
        355                 360                 365

Leu Lys Ser Asn Pro Val Gly Phe Asn Gly Val Ala Phe Lys Val Ala
    370                 375                 380

Gly Gly Leu Pro Ser Gly Met Pro Leu Thr Ser Asn Ser Leu Asn His
385                 390                 395                 400

Cys Leu Met Val Gly Cys Ala Val Thr Lys Ala Leu Glu Asp Ser Gly
                405                 410                 415

Val Gln Val Thr Trp Asn Phe Asp Ser Met Asp Leu Phe Thr Tyr Ala
            420                 425                 430

Asp Gly Val Tyr Val Pro Pro Leu Ser Ser Val Met Pro Lys Val Phe
        435                 440                 445

Ala Asn Leu Arg Gln Phe Gly Leu Lys Pro Thr Arg Thr Asp Lys Thr
    450                 455                 460

Asp Ala Glu Thr Pro Pro Ala Asp Glu Pro Val Glu Phe Leu Lys Arg
465                 470                 475                 480

Thr Leu Val Arg Thr Glu Asn Gly Arg Ala Leu Leu Asp Lys Ser Arg
                485                 490                 495

Gln Phe Tyr Tyr Lys Ala Glu Asn Thr Glu Glu Trp Thr Lys Pro Pro
            500                 505                 510

<210> SEQ ID NO 13
<211> LENGTH: 516
<212> TYPE: PRT
<213> ORGANISM: Caliciviridae

<400> SEQUENCE: 13

Lys Arg Phe Lys Asp Lys Trp Gly Tyr Phe Gln Ala Glu Gln His Pro
1               5                   10                  15

Pro Asn Cys Cys Ser Ser Arg Asn Ile Gln Thr His Gly Pro Met Gly
            20                  25                  30

Lys Pro Ser Val His Arg Leu Ala Ile Gln Arg His His Trp Thr His
```

-continued

```
                35                  40                  45
Leu Trp Cys Phe Ser Ile Ile Leu Phe Leu Asn Pro Gly Asp Cys
        50                  55                  60

Gly Leu Pro Tyr Thr Asp Glu His Gly Val Val Gly Leu His Ala
 65                  70                  75                  80

Gly Ser Gly Gly Asp Lys Cys Pro Ser Arg Lys Leu Val Pro Tyr
                 85                  90                  95

Val Lys Val Asp Met Lys Arg Asp Thr Cys Thr Lys Glu Tyr Lys Asp
                100                 105                 110

Asn Gln Pro Ser Tyr Lys Gly Leu Val Lys Glu Thr Gly Asp Pro
            115                 120                 125

Arg Thr Ile Met Lys Gly Thr Arg Leu His Val Ser Pro Ala His Thr
130                 135                 140

Gly Asp Tyr Glu Glu Cys Ser His Gln Pro Ala Ser Leu Gly Ala Gly
145                 150                 155                 160

Asp Pro Arg Cys Pro Ser Leu Thr Gly Met Val Asn Asn Leu Pro Tyr
                165                 170                 175

Thr Glu Ala Ala Pro Gly Pro Asp Thr Ser Thr Leu Asn Arg Val Ser
            180                 185                 190

Lys Met Leu Thr Thr Met Glu Gly Tyr Val Pro Lys Val His Lys Thr
            195                 200                 205

Glu Glu Asp Met Leu Ser Ala Phe Tyr Met Leu Asn His Asp Thr Ser
210                 215                 220

Cys Gly Pro Tyr Gly Gly Arg Lys Lys Asp His Val Lys Asp Gly Val
225                 230                 235                 240

Leu Lys Ala Leu Leu Asp Leu Leu Ser Ser Lys Trp Asn Arg Ala Lys
                245                 250                 255

Leu Gly Leu Ala Leu Pro His Glu Tyr Ala Leu Gly Leu Lys Asp Glu
            260                 265                 270

Leu Arg Pro Lys Asp Lys Val Ala Val Gly Lys Arg Arg Leu Trp Gly
        275                 280                 285

Cys Asp Val Gly Val Ser Thr Val Cys Ala Ala Phe Lys Arg Val
    290                 295                 300

Ser Glu Ser Met Asn His Ala Leu Gly Phe Gln Val Gly Asn Met Asp
305                 310                 315                 320

Gly Pro Ala Val Glu Asp Leu Phe Lys Glu Ala Gly Lys Thr Ala Arg
                325                 330                 335

Pro Val Leu Cys Leu Leu Gln Val Gly Phe Asn Ser Ala Thr Lys Ser
            340                 345                 350

Tyr Pro Asn His Thr Gln Ala Leu His Gln Ser Asn Cys Phe Gly Cys
            355                 360                 365

Tyr Ala Gln Val Lys Pro Ser Trp His Leu Gln Trp Arg Gly Val Gly
        370                 375                 380

Cys Gly Trp Thr Thr Val Trp Tyr Ala Thr His Phe His Gln Leu
385                 390                 395                 400

Thr Glu Ser Leu Ser His Gly Arg Leu Cys His Gly Ser Arg Gly
                405                 410                 415

Leu Arg Arg Ala Gly Asp Leu Glu His Leu Arg Leu Asp Gly Pro Val
            420                 425                 430

Tyr Leu Arg Arg Cys Leu His Arg Pro Thr Ser His Leu Phe Cys His
        435                 440                 445

Ala Gln Ser Leu Cys Glu Pro Thr Thr Val Arg Pro Glu Thr Asp Pro
450                 455                 460
```

```
Asp Arg Asn Gly Cys Asp Asn Ala His Pro Cys Arg Thr Ser Val Ser
465                 470                 475                 480

Gln Thr Asn Thr Cys Pro Asn Glu Trp His Thr Ser Thr Ser Gly Gln
                485                 490                 495

Asn Asn Ser Ala Val Leu Leu His Gln Ser Arg Glu His Arg Gly Met
            500                 505                 510

Asp Gln Thr Ala
        515

<210> SEQ ID NO 14
<211> LENGTH: 300
<212> TYPE: DNA
<213> ORGANISM: Caliciviridae

<400> SEQUENCE: 14
aaaagattta aagataaatg gtgaattggc tactttcagg ctgaacagca ccctcccaac       60
tgctgttcca gtcggaacat ccaaacccat taaggaccca tggggaaacc cagtgtccac      120
agattggcaa ttcaaagaat ttaacaccac atctggacac atctatggtg cttcagcatc      180
atcctgttcc ttaacccgcc aggtgattgt gggctaccat acaccgacga acacggtgtt      240
gtggtgggcc tgcatgcggg atcgggtggt gacaagtgcc cctcgcgtaa actcgtcgta      300
```

DIAGNOSIS, PREVENTION AND TREATMENT OF CALICIVIRUS INFECTION IN HUMANS

CROSS-REFERENCE TO RELATED APPLICATIONS

This claims the benefit of U.S. Provisional Application No. 60/118,209, filed Feb. 1, 1999.

FIELD OF THE INVENTION

The invention relates to caliciviruses, which are newly recognized as potentially important human pathogens. In a population of adult blood donors from Oregon, 18% were found to exhibit caliciviruses-specific antibodies.

BACKGROUND

Viruses of the family Caliciviridae are non-enveloped single stranded positive sense RNA viruses having a genome of about 8 Kbs in size. The capsid protein is a single molecular species of about 60 KDa and forms 22 cups or calyxs on the viral surface thereby providing the morphologic basis for the name Caliciviridae. Viruses of the calicivirus family have been known to be pathogenic in mammals since at least 1932 when they were shown to be the causative agent of vesicular exanthema of swine (VES). Subsequently, caliciviruses have been shown to be pathogens for cats and marine mammals, such as sea lions.

The family of Caliciviridae is divided into four taxonomic genera: Norwalk viruses and Sapporo viruses (both of which are gastrointestinal pathogens in humans), rabbit hemorrhagic disease viruses and vesiviruses. The first three of these genera all have proven refractory to in vitro cell culture replication. The fourth genus, the vesiviruses, may be replicated in cell culture, for instance using Vero cells. Despite the fact that caliciviruses have been known for many years as pathogens of mammals, cultivatable caliciviruses have not been found to be of clinical significance in the human population. In particular, vesiviruses have not shown to be significant infectious agents for humans.

Serologic evidence can suggest that animal viruses are also human pathogens and occasionally this is confirmed by a single case as was reported for Cache Valley virus [3]. Other times, with no prior warning, a single case signals the arrival of a new zoonotic disease as occurred with the death of a horse trainer in Australia infected with a previously unknown morbillivirus [4]. Such events can occur when shifts in ecologic relationships cause intermixing of species and result in increased "viral traffic" [5]. In turn, "viral traffic" encourages adaptive shifts in viral genomes and host-parasite relationships which can result in emerging new diseases, especially zoonoses [5]. An increase in viral traffic for one calicivirus has been deliberate in Australia, where hemorrhagic virus of rabbits [6, 7, 8] has been spread as a biologic control agent, resulting in a continent-wide calicivirus challenge of naive and diverse populations.

The early detection of, and appropriate responses to, emerging viral diseases that may result from events that heighten viral traffic require preventive programs involving research, early diagnosis, public health awareness and reporting.

SUMMARY

The invention concerns reagents and methods of detecting calicivirus in humans. The invention also provides calicivirus nucleic acid sequences and amino acid sequences that are useful for developing immunostimulatory polypeptides. As will be made clear by the specification, calicivirus infection is linked to human diseases, reproductive dysfunctions, and moreover calicivirus in humans may be transmitted via blood.

It has been discovered that caliciviruses are common infective agents in humans and can cause a serious vesicular disease characterized by fever, generalized myalgia and painful blistering of the hands and feet and a new strain of calicivirus (belonging to the vesivirus genus), that is called "San Miguel sea lion virus 5 serotype Homosapien-1" (SMSV-5 Hom-1) has been discovered and isolated. This disclosure is directed towards methods of detecting an infective agent in a sample from a human comprising detecting calicivirus antigens and/or anti-calicivirus antibodies; to methods of stimulating immune responses in human subjects against caliciviruses; and to SMSV-5 Hom-1, its polynucleotides and polypeptides.

One aspect of the present invention is a method of detecting a past (or present) infection of a human by an infectious viral agent comprising detecting anti-calicivirus antibodies in a sample from the putatively infected human subject. Another aspect of the present invention is a method of detecting a present viral infection of a human comprising detecting one or more calicivirus antigens and/or calicivirus genomic segments in a sample taken from the putatively infected human subject. A further aspect of the present invention is the provision of a protective vaccine against caliciviruses comprising inoculating a human subject with a vaccine comprising at least one calicivirus antigen or its cDNA sequence with a vector comprising a recombinant caliciviral polynucleotide wherein the viral vector expresses at least one calicivirus antigen.

Another aspect relates to nucleotides of SMSV-5 Hom-1, some of which may be used as probes or primers, for instance for use in detecting or amplifying viral polynucleotides. Yet another aspect relates to proteins of SMSV-5 Hom-1, which may be antigenic, some of which may be used in diagnostic and immune stimulatory applications such as the creation of vaccines. The invention also relates to antibodies specific for SMSV-5 Hom-1, which in certain embodiments may be monoclonal antibodies. Also included are assays to detect antigens of SMSV-5 Hom-1. Additionally, the invention includes assays to detect antibodies specific for SMSV-5 Hom-1. A further aspect of the invention relates to vaccines against SMSV-5 Hom-1 infection. All these different embodiments are discussed in detail below.

SEQUENCE LISTINGS

The nucleic and amino acid sequences listed in the accompanying sequence listing are shown using standard letter abbreviations for nucleotide bases, and three-letter code for amino acids. Only one strand of each nucleic acid sequence is shown, but the complementary strand is understood to be included by any reference to the displayed strand.

SEQ ID NO: 1 shows the nucleic acid sequence of the SMSV-5 Hom-1 RNA polymerase region.

SEQ ID NO: 2 shows the amino acid sequence of the SMSV-5 Hom-1 RNA polymerase region.

SEQ ID NO: 3 shows the nucleic acid sequence (1671 bases) of the p5RT73 genomic segment of SMSV-5.

SEQ ID NO: 4 shows a cDNA that encodes an amino acid sequence that is useful for detecting caliciviral specific binding agents.

SEQ ID NO: 5 shows the amino acid sequence encoded by the cDNA of SEQ ID NO: 4.

SEQ ID NOS: 6–10 show PCR primers.

SEQ ID NOS: 11–13 show the three possible ORFs of the nucleic acid sequence shown in SEQ ID NO: 3.

SEQ ID NO: 14 shows the nucleic acid sequence of a 300 bp probe that can be used to detect a broad range of caliciviruses.

BRIEF DESCRIPTION OF THE DRAWINGS

FIG. 4 is a graph comparing the nucleotide and predicted amino acid sequences of prototype SMSV-5 (SEQ ID NO: 2), PCV Pan-1 and SMSV-5 Hom-1 in the RNA polymerase gene region. SMSV-5 Hom-1 has 97% nucleotide and 96% amino acid identity with the prototype SMSV-5 and 85% nucleotide and 92% amino acid sequence identity with Pan-1 in this most highly conserved region of calicivirus genomes. These differences are consistent with the SMSV-5 Hom-1's designation as a strain of SMSV-5 [11]. The following GenBank accession numbers have been assigned to these sequences: SMSV-5 [U52093], SMSV-5 Hom-1 [U62327], and Pan-1 [U52086].

FIGS. 6A–6B is a list showing the cDNA sequence (SEQ ID NO: 3) of the p5RT73 genomic segment shown in FIG. 9.

FIGS. 7A–7F is a list showing the translation in three forward reading frames of the nucleic acid sequence shown in FIGS. 6A–6B (SEQ ID NOS: 11–13).

FIGS. 8A–8D is a list showing the cDNA sequence and amino acid sequence for group reactive caliciviral antigen for antibody detection 6 (SEQ ID NOS: 4–5).

FIG. 10 is a list showing the translated amino acid sequence comparison of SMSV-5 to other published calicivirus amino acid sequences within the 3C-like cysteine protease region of the non-structural protein of caliciviruses. SMSV-5 was compared to: FCV, feline calicivirus (155); RHDV, rabbit hemorrhagic disease virus (145); and SV, Southampton virus, a Norwalk-like virus, (122). Carats (ˆ) above amino acid residues represent the putative catalytic sites of the protein. Asterisks (*) under the sequences represent the number of caliciviruses which have identical amino acid residues to SMSV-5.

FIG. 11 is a list showing the translated amino acid sequence comparison of SMSV-5 (SEQ ID NO: 2) to other published calicivirus amino acid sequences within the RNA-dependent RNA polymerase region of the non-structural protein of caliciviruses. The symbols, and origin of comparison sequences are as in FIG. 10.

FIG. 12 is a table showing monoclonal antibodies used to identify neutralizing epitopes for vaccines.

FIG. 13 is a table showing monoclonal antibodies reactive with nearly all variants of the vesicular genus.

FIG. 14 is a table that shows the reactivity of polyclonal antibody sera with various antigen pools. The virus types for each pool are shown at the bottom of the corresponding column.

DETAILED DESCRIPTION

OVERALL DESCRIPTION OF VARIOUS EMBODIMENTS

Figure 1:
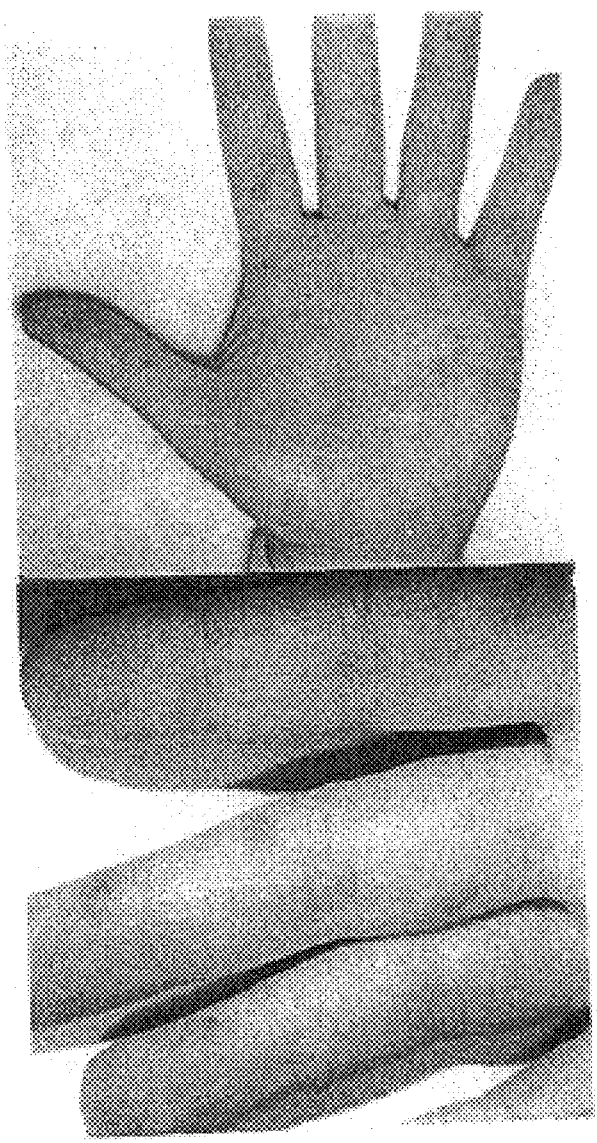
FIG. 1 is a photograph showing hand lesions from which SMSV-5 Hom-1 was isolated.

Caliciviruses are common infective agents in the human population (18% of the population sampled) and these infective viruses may be important in producing human disease. A human disease caused by calicivirus is characterized by fever, generalized myalgia and painful blistering of the hands and feet. Because of the prevalence of caliciviruses in the human population and their ability to produce disease, it would be desirable to have compositions and methods that would allow for the detection of calicivirus antigen and/or calicivirus antibody in a sample from a human. It would also be desirable to produce a vaccine that would protect a human against a caliciviral infection.

One aspect of the present invention is a method of detecting a past (or present) infection of a human by an infectious viral agent comprising detecting anti-calicivirus antibodies in a sample from the putatively infected human subject. Calicivirus antigens (recombinant or otherwise) can be used as substrate reagents in immunoassays to identify antibodies to caliciviruses in a sample, e.g., blood, as one means of determining if the sampled individual has been exposed to (or is currently infected with) a calicivirus, and to determine the concentration of the antibodies in the sample. The immunoassays in which such antigens can be used include, but are not limited to, radioimmunoassay, competition immunoprecipitation, enzyme-linked immunoadsorbent assay, virus neutralization, immunofluorescence assay and the like. The antigens used in such assays may comprise whole infective, attenuated or killed viral particles, or one or more native or recombinant caliciviral epitopes, antigenic subunits or haptens. Hapten molecules may be combined with a carrier molecule to produce antigenicity. The caliciviral antigens may be used in assay compositions in a concentration sufficient to form a detectable complex with specific antibodies. The caliciviral antigens can be mixed with or attached to a suitable matrix (support) or carrier, such as a latex particle or plastic microtiter plate or the like. They can also be conjugated with an enzyme, dye, radio-labeled or the like, depending upon what immunological method is used. The details of conducting various types of immunoassays is well known in the art and also described in *Antibodies* which is a *A Laboratory Manual* by Harlow and Lane, Cold Spring Harbor Laboratory (1988).

Another aspect of the invention is a method of detecting a present viral infection of a human by detecting one or more calicivirus antigens in a sample taken from the putatively infected human subject. Anti-calicivirus antibodies may be made and purified by conventional methods (Antibodies may be produced using standard procedures described in a number of texts, including *Antibodies, A Laboratory Manual* by Harlow and Lane, Cold Spring Harbor Laboratory, 1988) and may be polyclonal or monoclonal antibodies. Such antibodies may be used in quantitative and qualitative assays for antigens wherein the antibodies are contacted with a sample that putatively contains calicivirus antigens, wherein the antigens and the antibodies specifically bind to each other, and wherein the amount of antibody-antigen conjugate is then detected and measured.

A further aspect of the present invention is the provision of a protective vaccine against caliciviruses comprising inoculating a human subject with a vaccine comprising at least one calicivirus antigen or with a viral vector comprising a recombinant caliciviral polynucleotide wherein the viral vector, when inoculated into a human, expresses at least one calicivirus antigen. The methods of preparing such vaccines and vaccine vectors is more thoroughly discussed below in relation to SMSV-5 Hom-1, and methods discussed in relation to SMSV-5 Hom-1 vaccines are equally applicable to any calicivirus vaccine.

With reference to SMSV-5, the invention encompasses isolated polynucleotides derived from SMSV-5 genome, a 1671 base pair portion of which is shown in FIGS. 6A–6B (SEQ ID NO: 3), and the identified ORFs (open reading frames; SEQ ID NOS: 11–13) of this genome (for example 5rt73bp 1–300 (SEQ ID NO: 14) and 300–1671). Also included within the invention are oligonucleotides comprising at least 15, 20, 30, 40, 50, 70, 100 and 150 consecutive nucleotides of the sequence as shown in FIGS. 6A–6B.

The invention further includes nucleic acids encoding SMSV-5 Hom-1 amino acid sequences, such as those amino acid sequences shown in FIGS. 7A–7F, as well as recombinant nucleic acids that may include a promoter operably linked to a nucleic acid that encodes an SMSV-5 Hom-1 amino acid sequence.

Additionally included are isolated nucleic acid molecules of various defined lengths that show at least 50%, 60%, 70%, 80%, 90%, 95% or 99% sequence identity with at least a part of the nucleotide sequence as shown in FIGS. 6A–6B when compared using the BLASTN™ software (further discussed herein) using default parameters.

The invention also includes isolated nucleic acid molecules of various defined lengths that hybridize with at least a part of the nucleic acid sequence as shown in FIGS. 6A–6B (SEQ ID NO: 3). Generally, hybridization conditions are classified into categories, for example very high stringency, high stringency, and low stringency. The conditions for probes that are about 600 base pairs or more in length are provided below in three corresponding categories.

Very High Stringency (detects sequences that share 90% sequence identity

| Hybridization in | SSC at | 65° C. | 16 hours |
| Wash twice in | SSC at | room temp. | 15 minutes each |
| Wash twice in | SSC at | 65° C. | 20 minutes each |

High Stringency (detects sequences that share 80% sequence identity or greater)

| Hybridization in | SSC at | 65° C.–70° C. | 16–20 hours |
| Wash twice in | SSC at | room temp. | 5–20 minutes each |
| Wash twice in | SSC at | 55° C.–70° C. | 30 minutes each |

Low Stringency (detects sequences that share greater than 50% sequence identity)

| Hybridization in | SSC at | room temp. –55° C. | 16–20 hours |
| Wash twice in | SSC at | room temp. –55° C. | 20–30 minutes each |

Methods for preparing and using probes and primers are described in the references, for example Sambrook et al. Molecular Cloning: A Laboratory Manual, 2nd ed., Cold Spring Harbor Laboratory Press, New York, 1989; Ausubel et al. Current Protocols in Molecular Biology, Greene Publishing Associates and Wiley-Intersciences, 1987; and Innis et al., *PCR Protocols, A Guide to Methods and Applications*, Academic Press, Inc., San Diego, Calif. 1990. PCR primer pairs can be derived from a known sequence, for example, by using computer programs intended for that purpose such as Primer (Version 0.5, 1991, Whitehead Institute for Biomedical Research, Cambridge, Mass.).

Also within the invention are cells and virions that contain the nucleic acid molecules as described above. Such nucleic acids may be present in recombinant form, for instance, cloned into an expression vector. Cells may be transformed with a cloned recombinant nucleic acid of the invention in order to facilitate expression of a particular protein, such as that shown in FIGS. 8A–8D (SEQ ID NO: 5). Various vector systems are discussed below under "Cloning and Expression of SMSV-5 Hom-1 Nucleotides." Viruses may be engineered to contain the nucleic acids of the invention in order to produce a vaccine. Such viral vectors are discussed below under "Therapeutic Uses of SMSV-5 Hom-1 Nucleic Acids and Proteins."

Recombinant molecules are also encompassed within the bounds of the invention, and include, for instance, a nucleic acid molecule encoding a polypeptide as shown in FIGS. 8A–8D (SEQ ID NO: 4) linked to a non-native nucleic acid sequence such as a promoter. The nucleic acid molecule linked to the promoter may be all or part of an ORF as shown in FIGS. 7A–7F (SEQ ID NOS: 11–13; and 8 (SEQ ID NO: 5), or may be one or more fragments of a DNA sequence as shown in FIGS. 6A–6B (SEQ ID NO: 3).

Purified proteins (also called polypeptides) and fragments thereof are also included within the invention. These proteins may be proteins encoded by any of the claimed nucleic acid sequences, or may be the protein or a fragment of the proteins shown in FIGS. 7A–7F and 8A–8D (SEQ ID NOS: 11–13 and 5). Proteins and protein fragments of the invention may be of various sizes, for instance 5, 10, 15, 20, 30, 40, 50, 60 or even 100 amino acids or more in length.

The scope of the invention also encompasses Immunogenic polypeptides (also referred to as immunogenic (or antigenic) amino acid sequences) that are derived from SMSV-5 Hom-1 and that promote an immunological response when introduced into a mammal under suitable conditions for eliciting such a response (Better and Horowitz, 1990, *Advances in Gene technology: The Molecular Biology of Immune Disease & the Immune Response* (ICSU Short Reports); and Better et al., 1989, *Methods in Enzymology* 178: 176–496). In one embodiment, the present invention is directed to a vaccine composition comprising a pharmaceutically acceptable vehicle and at least one SMSV-5 Hom-1 antigen, which antigen may be any SMSV-5 Hom-1 antigen including, for example a recombinant subunit antigen e.g., those epitopes bound specifically by cross reactive monoclonal neutralizing antibodies (FIG. 12). Alternatively, whole attenuated SMSV-5 Hom-1 virus particles may be used in a vaccine composition. A recombinant subunit antigen may comprise one or more neutralizing epitopes of a SMSV-5 Hom-1 protein or glycoprotein. The protein may be selected from the group consisting of, for example either structural or non structural caliciviral proteins.

In one embodiment, the invention comprises assays for the detection of anti-SMSV-5 Hom-1 antibodies. SMSV-5 Hom-1 virus antigens or recombinant antigens of SMSV-5 Hom-1 can be used as substrate reagents in immunoassays to identify antibodies to SMSV-5 Hom-1 in a sample, e.g., blood, as one means of determining if the sampled individual has been exposed to (or is currently infected with) SMSV-5 Hom-1 and to determine the concentration of the antibodies in the sample. The immunoassays in which such antigens can be used include, but are not limited to, radioimmunoassay, competition immunoprecipitation, enzyme-linked immunoadsorbent assay, immunofluorescence assay and the like. The antigens of SMSV-5 Hom-1 for example those shown in FIGS. 4 (SEQ ID NO: 2) and FIGS. 6A–6B and 8A–8D (SEQ ID NOS: 5 and 11–13) or derived from SMSV-5 Hom 1 may be used in assay compositions in a concentration sufficient to form a detectable complex with specific antibodies. The SMSV-5 Hom-1 antigens can be mixed with or attached to a suitable matrix (support) or carrier, such as a latex particle or plastic microtiter plate or the like. They can also be conjugated with an enzyme, dye, radio-labeled or the like, depending upon what immunological method is used. The details of conducting various types of immunoassays is well known in the art and also described in *Antibodies. A Laboratory Manual* by Harlow and Lane, Cold Spring Harbor Laboratory (1988), the disclosures of which are incorporated by reference.

Figure 5:
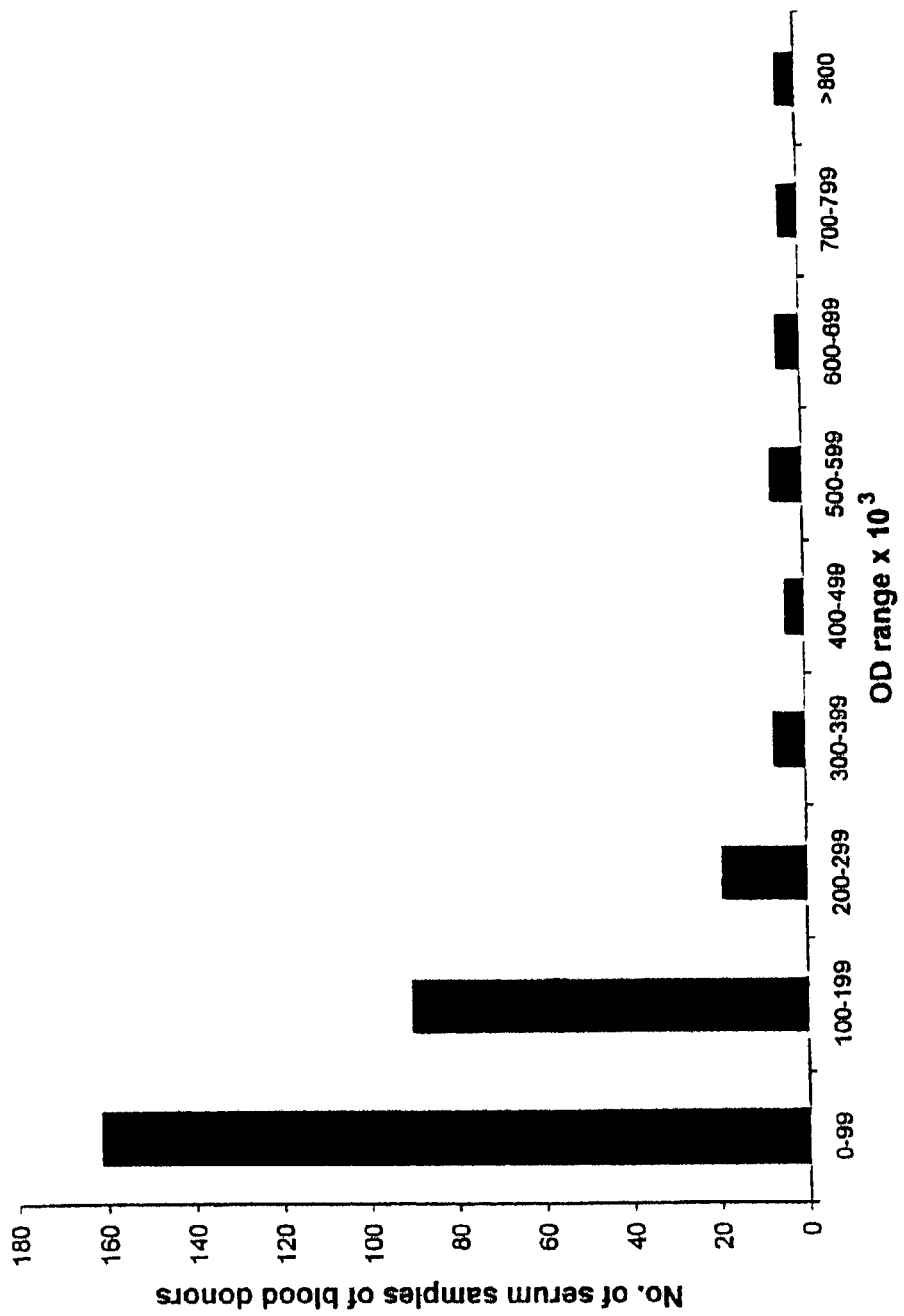
FIG. 5 is a graph showing the distribution of optical density values among adult blood donors in Portland, Oregon in an ELISA for antibody to SMSV caliciviruses. 18% of 300 blood donor sera collected over a six-month period show high levels of reactivity at OD value>0.20 (8% at OD>0.50).
Figure 9:
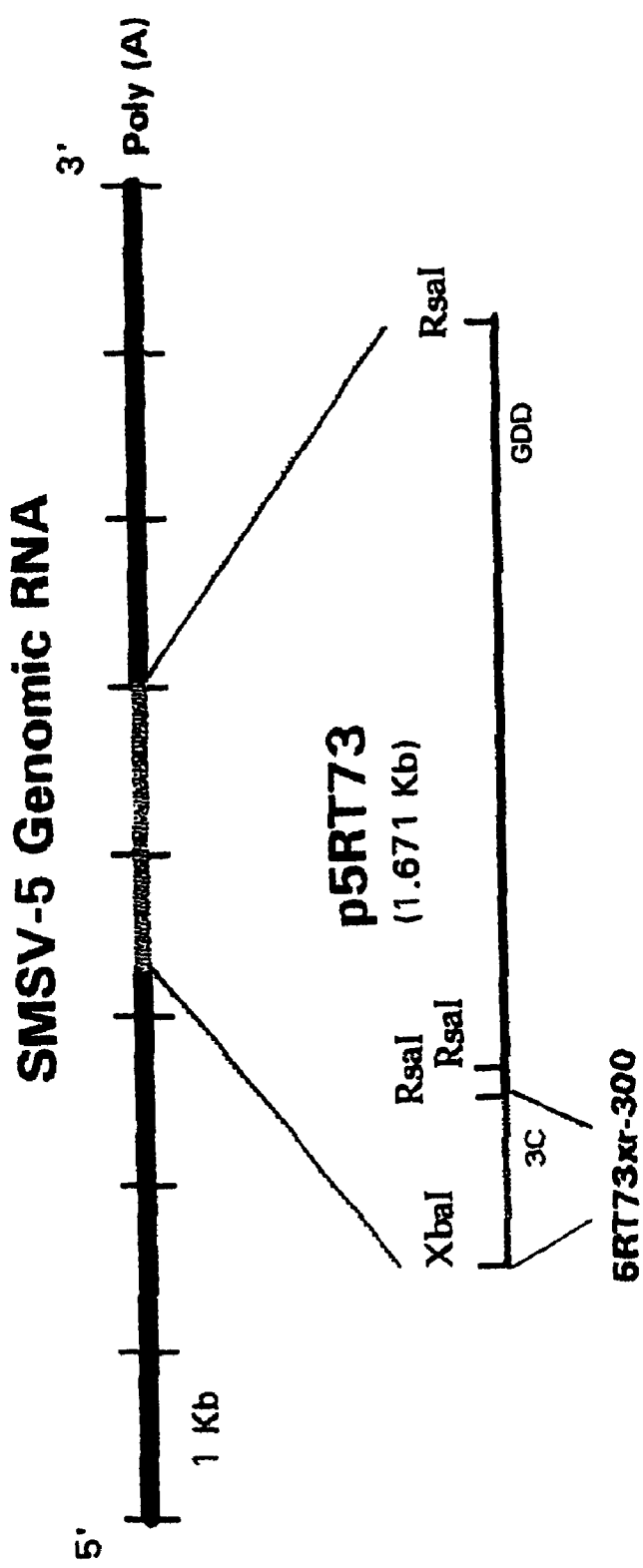
FIG. 9 is a list showing the genomic location and size of p5RT73 within the calicivirus genome, as well as the restriction map and location of the 5RT73xr-300 probe used in the hybridization experiments. The 3C-like cysteine protease region (3C) and the RNA-dependent RNA polymerase region (GDD) are also indicated.

Accordingly, the invention includes a method for determining the presence or absence of or concentration of antibodies for SMSV-5 Hom-1 in a sample by employing an immunoassay, the immunoassay characterized by using one or more non-recombinant or recombinant antigenic SMSV-5 Hom-1 polypeptides (FIG. 5) that bind with anti-SMSV-5 Hom-1 antibodies as a reagent in the immunoassay, whereby a complex of the anti-SMSV-5 Hom-1 antibodies and the SMSV-5 Hom-1 antigens is formed, and determining the presence or absence of or concentration of the complex formed as indicative of the presence or absence of or concentration of the antibodies.

In one embodiment, the invention comprises assays for detection of SMSV-5 Hom-1 antigens by using anti-SMSV-5 Hom-1 antibodies (for example FIG. 13). Anti-SMSV-5 Hom-1 antibodies may be made and purified by conventional methods (Antibodies may be produced using standard procedures described in a number of texts, including *Antibodies, A Laboratory Manual* by Harlow and Lane, Cold Spring Harbor Laboratory, 1988) and may be polyclonal or monoclonal antibodies. Such antibodies may be used in quantitative and qualitative assays for antigens wherein the antibodies are contacted with a sample that putatively contains SMSV-5 Hom-1 antigens, wherein the antigens and the antibodies specifically bind to each other, and wherein the amount of antibody-antigen conjugate is then detected and measured.

DEFINITIONS

The following terms are used herein to have the meanings noted below.

Calicivirus: The family Caliciviridae comprises a group of morphologically distinct viruses with an unusually diverse host spectrum, both phylogenetically and geographically. Caliciviruses are small (29–37 nm), non-enveloped, icosahedral viruses with T=3 lattice symmetry, that possess unique cup-shaped surface structures which are readily identifiable under the electron microscope. The genome of the caliciviruses is comprised of a single molecule of polyadenylated, single-stranded RNA of positive polarity. These agents have been isolated from, or observed in, a phylogenetically diverse variety of marine and terrestrial organisms, and serotype specific neutralizing antibody titers suggest that many of these agents move freely, over great distances, between ocean and land. Caliciviruses have the potential to cause serious disease in a wide variety of animals, including humans, whenever they are introduced into a susceptible population.

Vesiviruses: The genus vesivirus is currently made up of the caliciviruses that have been cultivated in-vitro and all have a genomic organization distinct from the other three currently described genera of the family caliciverdae. The vesiviruses (5' to 3') have three open reading frames coding (from 5' to 3') for non-structural (including polymerase), structural (including capsid) and VPg proteins.

SMSV-5 Hom-1: San Miguel sea lion virus 5 serotype Homosapien-1, isolated from a human subject (26). SMSV-5 Hom-1 may be grown on Vero cells, as described below, using standard virological techniques.

Antibodies: include intact antibodies as well as fragments thereof, such as Fab, Fab', $F(ab')_2$, and Fv which bind to an AIB1 epitope. These antibody fragments are defined as follows: (1) Fab, the fragment which contains a monovalent antigen-binding fragment of an antibody molecule produced by digestion of whole antibody with the enzyme papain to yield an intact light chain and a portion of one heavy chain; (2) Fab', the fragment of an antibody molecule obtained by treating whole antibody with pepsin, followed by reduction, to yield an intact light chain and a portion of the heavy chain; two Fab' fragments are obtained per antibody molecule; (3) $(Fab')_2$ the fragment of the antibody obtained by treating whole antibody with the enzyme pepsin without subsequent reduction; $F(ab')_2$, a dimer of two Fab' fragments held together by two disulfide bonds; (4) Fv, a genetically engineered fragment containing the variable region of the light chain and the variable region of the heavy chain expressed as two chains; and (5) single chain antibody ("SCA"), a genetically engineered molecule containing the variable region of the light chain, the variable region of the heavy chain, linked by a suitable polypeptide linker as a genetically fused single chain molecule. Methods of making these fragments are routine.

An antigen: refers to a molecule containing one or more epitopes that, when introduced into a host, will stimulate a host's immune system to make a humoral and/or cellular antigen-specific response. The term is also used interchangeably with "immunogen."

A subunit antigen: an antigen entity separate and discrete from a whole virus (live or killed). Thus, an antigen contained in a cell free extract would constitute a "subunit antigen" as would a substantially purified antigen.

An epitope: the site on an antigen or hapten to which a specific antibody molecule binds. The term is also used interchangeably with "antigenic determinant" or "antigenic determinant site."

A hapten: a molecule containing one or more epitopes that does not stimulate a host's immune system to make a humoral or cellular response unless linked to a carrier.

An immunological response: the development in the host of a cellular and/or antibody-mediated immune response to a composition or vaccine of interest. Usually, such a response consists of the subject producing antibodies, B cells, helper T cells, suppressor T cells, and/or cytotoxic T cells directed specifically to an antigen or antigens included in the composition or vaccine of interest.

Immunogenic polypeptide (or immunogenic amino acid sequence): refers to a polypeptide or amino acid sequence, respectively, which elicit antibodies that can participate in neutralizing viral infectivity, and/or mediate antibody-complement or antibody dependent cell cytotoxicity to provide protection of an immunized host.

The activity of the immunogenic polypeptide can be assayed using one of many assay that are well know in the art. Hence, the DNA sequences provided by this invention encode polypeptides that can stimulate T-cells to produce INF-γ. That is, these polypeptides act as epitopes for CD4 T-cells in the immune system. Studies have demonstrated that polypeptides isolated from an infectious agent and which are shown to be T-cell epitopes can protect against the disease caused by that agent when administered as a vaccine, Mougneau et al., *Science* 268:536–566, 1995 and Jardim et al., *J. Exp. Med.* 172:645–648, 1990. For example, T-cell epitopes from the parasite Leishmania major have been shown to be effective when administered as a vaccine, Jardim et al., *J. Exp. Med.* 172:645–648, 1990; Mougneau et al., *Science* 268:536–566, 1995; and Yang et al., *J. Immunology* 145:2281–2285, 1990. Therefore, the immunostimulatory polypeptides (T-cell epitopes) encoded by the DNA sequences according to the invention may be used, in purified form, as a vaccine.

An "immunogenic polypeptide" as used herein, includes the full length (or near full length) sequence of the desired protein (for instance, those eliciting a neutralizing antibody response (FIG. 12) or an immunogenic fragment thereof. By "immunogenic fragment" is meant a fragment of a polypeptide that includes one or more epitopes and thus elicits antibodies that neutralize viral infectivity, and/or mediates antibody-complement or antibody dependent cell cytotoxicity to provide protection of an immunized host. Such fragments will usually be at least about 5 amino acids in length, and preferably at least about 10 to 15 amino acids in length. There is no critical upper limit to the length of the fragment, which could comprise up to the full length of a protein sequence, or even a fusion protein comprising fragments of two or more subunit antigens.

Transformed: a transformed cell is a cell into which has been introduced a nucleic acid molecule by molecular biology techniques. The term encompasses all techniques by which a nucleic acid molecule might be introduced into such a cell, including transfection with viral vectors, transformation with plasmid vectors, and introduction of naked DNA by electroporation, lipofection, and particle gun acceleration.

Purified: the term purified does not require absolute purity; rather, it is intended as a relative term. Thus, for example, a purified protein preparation is one in which the subject protein or other substance is more pure than in its natural environment within a cell. Generally, a protein preparation is purified such that the protein represents at least 50% of the total protein content of the preparation.

Specific binding agent: a molecule that binds substantially only to a protein of interest when assessed using the methods described below. For instance, a molecule that binds specifically to a protein derived from 25 SMSV-5 Hom-1 is said to be a specific binding protein for the SMSV-5 Hom-1 protein. Such specific binding agents include antibodies that specifically bind to a protein of the present invention, as well as immunologically effective portions (fragments) thereof. These include, for instance, antibodies that bind specifically to the proteins shown in FIGS. 8A–8D (SEQ ID NO: 5). Specific binding agents that are capable of specifically binding to a protein of the invention may include polyclonal antibodies, monoclonal antibodies (including humanized monoclonal antibodies) and fragments of monoclonal antibodies such as Fab, F(ab')2 and Fv fragments, as well as any other agent capable of specifically binding to a protein of interest. For a review, see Better and Horowitz, 1990, *Advances in Gene technology: The Molecular Biology of Immune Disease & the Immune Response* (ICSU Short Reports). Antibodies may be produced using standard procedures described in a number of texts, including Antibodies, A Laboratory Manual by Harlow and Lane, Cold Spring Harbor Laboratory (1988).

Antibodies of the present invention may include humanized antibodies. Methods of making humanized monoclonal antibodies are well known, and include those described in U.S. Pat. No. 5,585,089 (Humanized Immunoglobulins), U.S. Pat. No. 5,565,332 (Production of Chimeric Antibodies—A Combinatorial Approach), U.S. Pat. No. 5,225,539 (Recombinant Altered Antibodies And Methods Of Making Altered Antibodies), U.S. Pat. No. 5,693,761 (Polynucleotides encoding Improved Humanized Immunoglobulins), U.S. Pat. No. 5,693,762 (Humanized Immunoglobulins), U.S. Pat. No. 5,585,089 (Humanized Immunoglobulins), and U.S. Pat. No. 5,530,101 (Humanized Immunoglobulins), and references cited therein.

Similarly, methods of making and using immunologically effective portions of monoclonal antibodies, also referred to as antibody fragments, are well known and include those described in Better and Horowitz, 1990, *Advances in Gene technology: The Molecular Biology of Immune Disease & the Immune Response* (ICSU Short Reports); and Better et al., 1989, *Methods in Enzymology* 178:176–496.; and U.S. Pat. No. 5,648,237 (Expression of Functional Antibody Fragments), U.S. Pat. No. 4,946,778 (Single Polypeptide Chain Binding Molecules), and U.S. Pat. No. 5,455,030 (Immunotherapy Using Single Chain Polypeptide Binding Molecules), and references cited therein.

Virion: a complete viral particle including envelope (if any), capsid, and nucleic acid elements.

Isolated: an isolated nucleic acid has been substantially separated or purified away from other nucleic acid sequences in the cell of the organism in which the nucleic acid naturally occurs, i.e., other chromosomal and extrachromosomal DNA and RNA. The term "isolated" thus encompasses nucleic acids purified by standard nucleic acid purification methods. The term also embraces nucleic acids prepared by recombinant expression in a host cell as well as chemically synthesized nucleic acids.

ORF: open reading frame. An ORF is a contiguous series of nucleotide triplets coding for amino acids. These sequences are usually translatable into a polypeptide.

Homologs: two nucleotide or amino acid sequences that share a common ancestral sequence and diverged when a species carrying that ancestral sequence split into two species. Homologs frequently show a substantial degree of sequence identity.

Nucleic acid sequence identity: refers to the degree to which two polynucleotide sequences possess identical nucleotides when compared using a standardized algorithm. Such an algorithm may insert, in a standardized and reproducible way, gaps in the sequences being compared in order to achieve a more meaningful comparison of the two sequences. The higher the percentage sequence identity between two sequences, the more similar the two sequences are said to be. Such similarity is frequently an indication of homology (i.e.: evolutionary relatedness).

A commonly used and freely available sequence comparison algorithm is the National Center for Biotechnology Information (NCBI) Basic Local Alignment Search Tool (BLAST) (Altschul et al., 1990), which is available from several sources, including the NBCI, Bethesda, Md. and on the Internet, for use in connection with the sequence analysis programs blastp (for proteins), blastn (for nucleotides), blastx, tblastn and tblastx. These tools are commonly used with gap and other parameters set to default settings. BLAST can be accessed at the NCBI website.

A pair of nucleic acids being compared, for instance from two evolutionarily related sequences, may have at least 50% sequence identity counted over the length of one of the nucleic acids (the reference nucleic acid) using the NCBI Blast 2.0.6, gapped blastn set to default parameters. Such a pair of nucleic acids may show, for example, at least 50%, 60%, 70%, 80%, 90%, 92%, 94, 95% or even 98% sequence identity.

Two nucleic acid sequences that show 50% or greater sequence identity will often encode polypolypeptides that are immunologically cross reactive with each other, i.e., antisera raised against one protein will cross react with antigens from the other protein.

Nucleic acids being compared may be of various lengths, for example, not less than 15, 25, 35, 45, 55, 65, 75 or 100 nucleotides in length. In some cases, entire genes may be compared, and in some cases, nucleotide fragments being compared may contain multiple genes and be hundreds or thousands of nucleotides in length.

Nucleic acid hybridization: Another indication that two nucleic acid sequences share a high degree of similarity, for example, 50% or greater, is that the two molecules hybridize to each other under defined hybridization conditions. The defined hybridization conditions may be more or less stringent, with more stringent conditions allowing less non-specific binding, i.e., binding between pairs of nucleic acid probes that are not perfectly matched.

Because the degree to which two nucleic acids will bind is dependent upon their sequences, stringency is sequence dependent. Generally, stringency of hybridization is expressed with reference to the temperature under which the wash step is carried out. Generally, such wash temperatures are selected to be about 5° C. to 20° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. An equation for calculating $T_m$ and conditions for nucleic acid hybridization is well known and can be found in Sambrook et al., 1989, *Molecular Cloning: A Laboratory Manual*, $2^{nd}$ ed., vol. 1–3, Cold Spring Harbor, N.Y.; specifically see volume 2, chapter 9.

Conditions for hybridization between nucleotides of the present invention (e.g., between two nucleotides showing substantial similarity) include wash conditions of 70° C. and about 0.2×SSC for 1 hour, or alternatively, 65° C., 60° C., or 55° C. and about 0.2 to 2×SSC (with, for instance, about 0.1% SDS) for 1 hour. Typically, blocking reagents are used to block non-specific hybridization. Such blocking reagents include, for instance, salmon sperm DNA. Hybridization, particularly under highly stringent conditions (e.g., wash temperatures of 60° C. or more and SSC concentrations of 0.2×) is suggestive of evolutionary similarity between the nucleotides. Such similarity (whether produced by convergent or divergent evolution) is strongly indicative of a similar role for the nucleotides and their resultant proteins.

Nucleic acid sequences that do not show a high degree of identity may nevertheless encode similar amino acid sequences due to the degeneracy of the genetic code. It is understood that changes in nucleic acid sequence can be made using this degeneracy to produce multiple nucleic acid sequence that all encode substantially the same protein. The length of nucleic acids being hybridized may vary widely and either the hybridization probe or the target sequence or both may be as short as 15 nucleotides or as long as several thousand nucleotides. Such nucleic acids are described, for example, under "Nucleic Acid Sequence Identity" above.

Sequence similarity: The similarity between two nucleic acids or two amino acid sequences is expressed in terms of percentage sequence identity. The higher the percentage sequence identity between two sequences, the more similar the two sequences are.

In the case of protein alignments, similarity is measured not only in terms of percentage identity, but also takes into account conservative amino acid substitutions. Such conservative substitutions generally preserve the hydrophobicity and acidity of the substituted residue, thus preserving the structure (and therefore function) of the folded protein. The computer programs used to calculate protein similarity employ standardized algorithms that, when used with standardized settings, allow the meaningful comparison of similarities between different pairs of proteins.

Sequences are aligned, with allowances for gaps in alignment, and regions of identity are quantified using a computerized algorithm. Default parameters of the computer program are commonly used to set gap allowances and other variables.

Methods of alignment of sequences for comparison are well-known in the art. Various programs and alignment algorithms are described by Pearson et al., *Methods in Molecular Biology* 24: 307–331, 1994, and in Altschul et al., *Nature Genet.* 6:119–129, 1994. Altschul et al. presents a detailed consideration of sequence alignment methods and homology calculations.

The NCBI Basic Local Alignment Search Tool (BLAST™) (Altschul et al., *J. Mol. Biol.* 215:403–410, 1990 is available from several sources, including the National Center for Biotechnology Information (NBCI, Bethesda, Md.) and on the Internet, for use in connection with the sequence analysis programs blastp, blast, blastx, tblastn and tblastx. BLAST™ can be accessed at the NCBI website. A description of how to determine sequence identity using this program is available at the web site. As used herein, sequence identity is commonly determined with the BLAST™ software set to default parameters. For instance, blastn (version 2.0) software may be used to determine sequence identity between two nucleic acid sequences using default parameters (expect=10, matrix=BLOSUM62, filter=

DUST (Tatusov and Lipmann, in preparation as of Dec. 1, 1999; and Hancock and Armstrong, *Comput Appl. Biosci.* 10:67–70, 1994), gap existence cost=11, per residue gap cost=1, and lambda ratio=0.85). For comparison of two polypeptides, blastp (version 2.0) software may be used with default parameters (expect 10, filter=SEG (Wootton and Federhen, *Computers in Chemistry* 17:149–163, 1993), matrix=BLOSUM62, gap existence cost=11, per residue gap cost=1, lambda=0.85).

When aligning short polypeptides (fewer than around 30 amino acids), the alignment should be performed using the Blast 2 sequences function, employing the PAM30 matrix set to default parameters (open gap 9, extension gap 1 penalties).

An alternative alignment tool is the ALIGN Global Optimal Alignment tool (version 3.0) available from Biology Workbench available at through a website maintained by the San Diego Supercomputing Center at the University of California San Diego. This tool may be used with settings set to default parameters to align two known sequences. References for this tool include Meyers and Miller, *CABIOS* 4:11–17, 1989.

Conservative amino acid substitutions: are those substitutions that, when made, least interfere with the properties of the original protein, i.e., the structure and especially the function of the protein is conserved and not significantly changed by such substitutions. The table below shows amino acids which may be substituted for an original amino acid in a protein and which are regarded as conservative substitutions.

| Original Residue | Conservative Substitution |
| --- | --- |
| ala | ser |
| arg | lys |
| asn | gln, his |
| asp | glu |
| cys | ser |
| gln | asn |
| glu | asp |
| gly | pro |
| his | asn, gln |
| ile | leu, val |
| leu | ile, val |
| lys | arg, gln, glu |
| met | leu, ile |
| phe | met, leu, tyr |
| ser | thr |
| thr | ser |
| trp | tyr |
| tyr | trp, phe |
| val | ile, leu |

Conservative substitutions generally maintain (a) the structure of the polypeptide backbone in the area of the substitution, for example, as a sheet or helical conformation, (b) the charge or hydrophobicity of the molecule at the target site, or (c) the bulk of the side chain.

The substitutions which in general are expected to produce the greatest changes in protein properties will be non-conservative, for instance changes in which (a) a hydrophilic residue, e.g., seryl or threonyl, is substituted for (or by) a hydrophobic residue, e.g., leucyl, isoleucyl, phenylalanyl, valyl or alanyl; (b) a cysteine or proline is substituted for (or by) any other residue; (c) a residue having an electropositive side chain, e.g., lysyl, arginyl, or histadyl, is substituted for (or by) an electronegative residue, e.g., glutamyl or aspartyl; or (d) a residue having a bulky side chain, e.g., phenylalanine, is substituted for (or by) one not having a side chain, e.g., glycine.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

Probe: An isolated nucleic acid attached to a detectable label or reporter molecule. Typical labels include radioactive isotopes, ligands, chemiluminescent agents, and enzymes.

Antisense, Sense, and Antigene: Double-stranded DNA (dsDNA) has two strands, a 5'→3' strand, referred to as the plus strand, and a 3'→5' strand, referred to as the minus strand. Because RNA polymerase adds nucleic acids in a 5'→3' direction, the minus strand of the DNA serves as the template for the RNA during transcription. Thus, the RNA formed will have a sequence complementary to the minus strand, and identical to the plus strand (except that U is substituted for T).

Antisense molecules are molecules that are specifically hybridizable or specifically complementary to either RNA or the plus strand of DNA. Sense molecules are molecules that are specifically hybridizable or specifically complementary to the minus strand of DNA. Antigene molecules are either antisense or sense molecules directed to a dsDNA target.

In the context viral genomes that are RNA the strand that encodes the polypeptide is considered the "plus-strand" and the non-coding strand, if present, is considered the minus strand. Thus, antisense molecules and/or antigene molecules can be designed to hybridize to either the "plus-strand" or the "minus-strand" of the viral nucleic acid.

Therapeutically effective calicivirus oligonucleotides and oligonucleotide Analogs: "Therapeutically effective oligonucleotides and oligonucleotide analogs" are characterized by their ability to inhibit the viral replication. Complete inhibition, however, is not necessary for therapeutic effectiveness. Therapeutically effective oligonucleotides and oligonucleotide analogs are characterized by their ability to inhibit viral replication. Inhibition can be measured by adding the oligonucleotides to cultured cells that have been or are subsequently infected with calicivirus. The level of viral replication can then be determined via northern blotting or ELISA. The results from the sample treated with the oligonucleotides can then be compared to the results from a control non-infected cell culture. The oligonucleotide is considered “therapeutically effective” if it inhibits viral replication when compared to the control. Additionally, some oligonucleotides will be capable of inhibiting the viral replication by at least 15%, 30%, 40%, 50%, 60%, or 70%.

Therapeutically effective oligonucleotides and oligonucleotide analogs are additionally characterized by being sufficiently complementary to a viral nucleic acid sequence. Sufficient complementary means that the therapeutically effective oligonucleotide or oligonucleotide analog can specifically disrupt viral replication.

Primers: Short nucleic acids, preferably DNA oligonucleotides 10 nucleotides or more in length, which are annealed to a complementary target DNA strand by nucleic acid hybridization to form a hybrid between the primer and the target DNA strand, then extended along the target DNA strand by a DNA polymerase enzyme. Primer pairs can be used for amplification of a nucleic acid sequence, e.g., by the polymerase chain reaction (PCR) or other nucleic-acid amplification methods known in the art.

Probes and primers as used in the present invention typically comprise at least 15 contiguous nucleotides of a known sequence. In order to enhance specificity, longer probes and primers may also be employed, such as probes and primers that comprise at least 20, 30, 40, 50, 60, 70, 80, 90, 100, or 150 consecutive nucleotides of the disclosed nucleic acid sequences.

Methods for preparing and using probes and primers are described in the references, for example Sambrook et al., 1989, Molecular Cloning: A Laboratory Manual, $2^{nd}$ ed., vol. 1–3, Cold Spring Harbor, N.Y.; Ausubel et al., 1987, Current Protocols in Molecular Biology, Greene Publ. Assoc. & Wiley-lntersciences; Innis et al., 1990, PCR Protocols, A guide to Methods and Applications. PCR primer pairs can be derived from a known sequence, for example, by using computer programs intended for that purpose such as Primer (Version 0.5, 1991, Whitehead Institute for Biomedical Research, Cambridge, Mass.).

Recombinant nucleic acid: a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques such as those described in Sambrook et al. (1989). The term recombinant includes nucleic acids that have been altered solely by addition, substitution, or deletion of a portion of the nucleic acid. Frequently, a recombinant nucleic acid may include a nucleic acid sequence operably linked to a promoter sequence. Such a recombinant nucleic acid may be part of a vector, used to transform a cell.

Alternatively, such a recombinant nucleic acids may be part of a viral vector, e.g., based on a vaccinia virus, that could be use to vaccinate a mammal wherein the recombinant nucleic acid is expressed, inducing a protective immunological response in the mammal.

METHODS

General Methods

The present invention utilizes standard laboratory practices for the cloning, manipulation and sequencing of nucleic acids, purification and analysis of proteins and other molecular biological and biochemical techniques, unless otherwise stipulated. Such techniques are explained in detail in standard laboratory manuals such as Sambrook et al., 1989, Molecular Cloning: A Laboratory Manual, $2^{nd}$ ed., vol. 1–3, Cold Spring Harbor, N.Y.; and Ausubel et al., 1987, Current Protocols in Molecular Biology, Greene Publ. Assoc. & Wiley-lntersciences.

Preparation of SMSV-5 Hom-1 Nucleic Acid Sequences

A. Obtaining the Viral Genome

The SMSV-5 Hom-1 genome of the invention may be procured by de-novo isolation from a viral culture. A biological sample of the virus was deposited with the American Type Culture Collection (ATCC) in Manassas, Va. on Oct. 16, 2002, under the requirements of the Budapest Treaty. This virus is available from the ATCC under accession number PTA-4762. This virus may be grown in vitro using Vero cell monolayers as described in the Examples below. The virus may be harvested from the culture supernatant and infected Vero cells. Cellular debris may be removed by centrifugation and intracellular virus particles may be released by sonication followed by centrifugation to pellet debris. The virus may then be pelleted by centrifugation and further purified through a CsCl gradient. The band containing the virus may be collected and the virus then pelleted by centrifugation. Viral RNA may be isolated by extraction with Trizol reagent (GIBCO-BRL, Gaithersburg, Mass.).

B. Obtaining Selected Polynucleotides from the Viral Genome

The isolated viral genome may be used as a source of polynucleotides as identified by the sequences disclosed herein (FIGS. 4, 6A–6B, 7A–7F, and 8A–8D; and SEQ ID NOS: 1, 3 and 4). The reverse-transcriptase polymerase chain reaction (RT-PCR) may be used to amplify any polynucleotide selected from the known viral sequence using the viral genome as a source of template RNA. The template RNA may also be provided in the form of the complete viral genome or one or more cosmids that contain fragments of the viral genome for example the clone with 5rt73 (FIGS. 6A–6B; and SEQ ID NO: 3). Actual RT-PCR amplifications of cDNA sequences have been carried out using primers, for example from a primate calicivirus as described below in the examples and FIG. 4.

The selection of PCR primers may be made according to the portions of the genome to be amplified. Primers may be chosen to amplify small fragments of the genome, ORFs or fragments including many contiguous genes from the genome. Variations in amplification conditions may be required to accommodate primers of differing lengths, and such considerations are well known in the art and are discussed in Innes at al, 1990, Sambrook et al, 1989, and Ausubel et al, 1987. For example, the ORF corresponding to that shown in FIG. 4 may be amplified from an SMSV-5 Hom-1 genomic (or appropriate cosmid) template using the following pair of primers (these primers correspond to nucleotide sequences outside of that shown in FIG. 4 (SEQ ID NO: 1):

5'-CGGGTCGGTTTCAGACCAAAC-3' (SEQ ID NO: 6)

5'-ATCCAAGTTGGCATCAAA-3' (SEQ ID NO: 7)

For the RT step, 5 µl of extracted nucleic acid was added to 0.2 µg primer and 10 units of avian myeloblastosis virus reverse transcriptase (Amersham Corp., Arlington Heights, Ill.) and the 50 µl reaction mixture was incubated for 1 h at 42° C. Next, 0.2 µg of the second primer and 5 units of Taq polymerase (Perkin-Elmer Cetus, Norwalk, Colo.) were added to the mixture to produce a final volume of 100 µl. Forty cycles of 1 min of denaturation at 94° C., 1 min of annealing at 37° C., and 1 min of primer extension at 72° C. were performed in thermal cycler (programmable Thermal Controller, M.J. Research, Inc., Cambridge, Mass.). Annealing temperatures were raised to obtain some products. The RT-PCR products were visualized by agarose gel electrophoresis.

Such primers are illustrative only and it will be readily appreciated by one of ordinary skill in the art that many different primers may be selected from the sequence disclosed and used in PCR amplification reactions to amplify cDNA sequences of interest from the SMSV-5 Hom-1 genome.

Polynucleotides that may be obtained by the above methods include, for example those shown in FIG. 4 (SEQ ID NO: 1). It is readily apparent that fragments of any length may be made using the above methods and information.

C. Cloning and Expression of SMSV-5 Hom-1 Nucleotides

Fragments amplified as described herein can be cloned into standard cloning vectors and expressed in commonly used expression systems consisting of a cloning vector and a cell system in which the vector is replicated and expressed.

Since calicivirus is a virus isolated from a mammal, eukaryotic vectors may be well suited to the expression of calicivirus derived genes, although prokaryotic vectors may also be used and may be well suited for high protein expression. A number of commercial protein expression and purification systems are widely available and may be used for expression and purification of calicivirus proteins.

Various yeast strains and yeast-derived vectors are commonly used for expressing and purifying proteins, for example, *Pichia pastoris* expression systems are available from Invitrogen (Carlsbad, Calif.). Such systems include suitable *Pichia pastoris* strains, vectors, reagents, transformants, sequencing primers and media. Available strains include a GS115 his 4 deficient strain, a KM71 aox1 deficient strain, a GS115 $His^+$ $Mut^-$ strain for extracellular expression and a $His^+$ $Mut^-$ strain for intracellular expression, all of which are available commercially from Invitrogen (Carlsbad, Calif.).

Non-yeast eukaryotic vectors may also be used for expression of the calicivirus proteins. Examples of such systems are the well known Baculovirus system, the Ecdysone-inducible mammalian expression system that uses regulatory elements from *Drosophila melanogaster* to allow control of gene expression, and the Sindbis viral expression system that allows high level expression in a variety of mammalian cell lines. These expression systems are also available from Invitrogen.

Standard prokaryotic cloning vectors may also be used, for example pBR322, pUC18 or pUC19 as described in Sambrook et al, 1989. Nucleic acids of calicivirus may be cloned into such vectors which may then be transformed into bacteria such as *Escherischia Coli* (*E. coli*) which may then be cultured so as to express the protein of interest. Other prokaryotic expression systems include, for instance, the arabinose-induced pBAD expression system that allows tightly controlled regulation of expression, the IPTG-induced pRSET system that facilitates rapid purification of recombinant proteins and the IPTG-induced pSE402 system that has been constructed for optimal translation of eukaryotic genes. These three systems are available commercially from Invitrogen and, when used according to the manufacturer's instructions, allow routine expression and purification of proteins.

The cloned expression vector may then be transformed into a particular cell type and the nucleotide expressed. Many different types of cell may be used to express the modified nucleic acid molecules.

Examples of such cells include cells of yeasts, fungi, insects and humans and plants, including transformed and non-transformed cells. For instance, common mammalian cells that could be used for the invention include human HeLa cells, SW-527 human cells (ATCC deposit #7940), WISH cells (ATCC deposit #CCL-25), Daudi cells (ATCC deposit #CCL-213), Mandin-Darby bovine kidney cells (ATCC deposit #CCL-22) and Chinese Hamster ovary cells (ATCC deposit #CRL-2092). Common yeast cells include *Pichia pastoris* (ATCC deposit #201178) and *Saccharomyces cerevisiae* (ATCC deposit #46024). Insect cells include cells from *Drosophila melanogaster* (ATCC deposit #CRL-10191), the cotton bollworm (ATCC deposit #CRL-9281) and from *Trichoplusia ni* egg cell homoflagelates. Fish cells that may be used include those from rainbow trout (ATCC deposit #CLL-55), salmon (ATCC deposit #CRL-1681) and Zebrafish (ATCC deposit #CRL-2147). Amphibian cells that may be used include those of the Bullfrog, *Rana catesbelana* (ATCC deposit #CLL-41). Reptile cells that may be used include those from Russell's Viper (ATCC deposit #CCL-140). Plant cells that could be used include Chlamydomonas cells (ATCC deposit #30485), Arabidopsis cells (ATCC deposit #54069) and tomato plant cells (ATCC deposit #54003). Many of these cell types are commonly used and are available from the ATCC as well as from commercial suppliers such as PHARMACIA™ and INVITROGEN™.

Expressed protein may be accumulated within a cell or may be secreted from the cell. Such expressed protein may then be collected and purified. This protein may then be characterized for activity and heat stability and may be used to practice the methods of the invention.

Production of an Antibody to Calicivirus Proteins

Antibodies may be produced to a calicivirus protein. Optimally, antibodies raised against the calicivirus protein will specifically detect (bind specifically with) the calicivirus protein and would not substantially recognize or bind to other proteins. The determination that an antibody specifically detects a SMSV-5 Hom-1 protein is made by any one of a number of standard immunoassay methods; e.g., the Western blotting technique (Sambrook et al., 1989). An antibody that is specific for a calicivirus protein will bind substantially only to the calicivirus protein on a Western blot, and will not show significant binding to unrelated proteins (e.g., from serum albumin). Antibodies that are capable of specifically binding to an calicivirus protein may include polyclonal antibodies, monoclonal antibodies (including humanized monoclonal antibodies) and fragments of monoclonal antibodies such as Fab, F(ab')2 and Fv fragments, as well as any other agent capable of specifically binding to an SMSV-5 Hom-1 protein.

Substantially pure calicivirus protein suitable for use as an immunogen may be obtained using an expression system as described above. Concentration of protein in the final preparation is adjusted, for example, by concentration on an Amicon filter device, to the level of a few micrograms per milliliter. Monoclonal or polyclonal antibody to the protein can then be prepared as described by Harlow and Lane, 1988, Antibodies, A Laboratory Manual, Cold Spring Harbor Press.

Alternatively, antibodies may be raised against synthetic calicivirus polypeptides synthesized on a commercially available polypeptide synthesizer based upon the predicted amino acid sequence of the SMSV-5 Hom-1 protein (Harlow and Lane, 1988).

Another method of raising antibodies against calicivirus proteins is by subcutaneous injection of a DNA vector which expresses the calicivirus protein into laboratory animals, such as mice. Delivery of the recombinant vector into the animals may be achieved using a hand-held form of the Biolistic system (Sanford et al., 1987, *Particulate Sci. Technol.* 5:27–37) as described by Tang et al. 1992, *Nature* (London) 356:152–154. Expression vectors suitable for this purpose may include those which express one or more calicivirus proteins under the transcriptional control of either the human β-actin promoter or the cytomegalovirus (CMV) promoter.

Antibody preparations prepared according to these protocols are useful in quantitative immunoassays which determine concentrations of antigen-bearing substances in biological samples; they are also used semi-quantitatively or qualitatively to identify the presence of antigen in a biological sample. FIG. 13 provides examples of monoclonal antibodies for such purposes and FIG. 14 provides polyclonal antibody examples.

Diagnostic Uses of SMSV-5 Hom-1 Proteins

Whole virus (CsCl purified) can be used as caliciviral specific protein for antibody detection (26) as can selected subgenomic expression products (FIG. 8; SEQ ID NO: 4).

The nucleic acid sequence (SEQ ID NO: 4) and the corresponding amino acid sequence (SEQ ID NO: 5) have been shown to be useful for detecting specific binding agents that bind to different calicivirus isolates. Therefore, the polypeptide shown in SEQ ID NO: 5, or fragments thereof, may be useful for screening samples from subjects that are thought to have been exposed to calicivirus.

Diagnostic Uses of SMSV-5 Hom-1 Antibodies

Type specific neutralizing antibodies can be used to identify specific virus isolates (26), polyclonal and monoclonal antibodies can serve as group specific test (FIGS. 13 & 14) for viral presence or for histochemical probes to detect virus in tissues or bodily samples.

Those reagents having utility for diagnosing and preventing vesiviral diseases and their application in humans as described in this disclosure would be expected to also have application for use in detecting and preventing vesivirus infections in animal species where these animals may be or may become reservoirs of vesiviruses posing a threat to human health. For instance, the vesivirus designated SMSV-17 which can be expected to have approximately 90% nucleotide homology with SMSV-5 Hom-1, has been isolated from edible shellfish (a marine mussel) and also from an aborted mammalian fetus (see Poet SE Detection and Isolation of Calicivirus from a Bivalve Mollusk [*Mytilus californianus*] Collected from Rocks Adjacent to Pinniped Rookeries Ph.D. Thesis, Oregon State University (1994) pages 77–98). In all, over 20 species of domestic animals, wildlife, zoologic species and poikilotherms such as fish, frogs and snakes have yielded vesivirus isolates that are now expected to pose a human health challenge either as food safety threats or by contact.

Therapeutic Uses of Calicivirus Nucleic Acids and Proteins

The calicivirus virus may be used to produce a vaccine that provides a protective immune response against calicivirus infection. Such vaccines may be monovalent or polyvalent. Such a vaccine may include whole virus particles that may be attenuated or killed by, for example chemical or heat treatment. Such a vaccine may also comprise immunogenic subunit antigens (epitopes) derived from calicivirus using whole attenuated live virus given by injection, nasal spray or orally or by other means to insure processing of appropriate antigens by immunocytic tissues. Attenuated viruses are those that have been adapted to alternate hosts and thus lose their disease causing properties yet retain some replicative ability in the target host. Examples would be chick embryo adapted vaccines for rabies. Alternatively whole virus inactivated but delivered properly and in sufficient quantities to stimulate immune response could be carried out as could selected antigenic components (subunits) of the virus delivered as "killed" vaccine. Subunits can also be rendered immunogenic by incorporating them into live vector systems (for example vaccinia virus) where the replicating vaccinia virus produces the desired recombinant antigen, for example a Sindbis virus neutralizing antibody producing epitope or epitopes was expressed by vaccinia virus in cattle and in turn they elicited antibody that neutralized Sindbis virus (*See Franke et al "Immunization of cattle with a recombinant Togavirus-vaccinia virus strain." *Res Vet Sci* 1985 39:113–115). A second example is the rabies vaccines administered as live vaccinia virus recombinants to wildlife. Another example of viral vectors for live virus vaccines are the herpesviruses and there are others. Yet other systems include insect viruses (for example, Baculovirus) used for producing large quantities of protein from a recombinant insert. Expressed protein is then purified and used as a vaccine. Finally, so-called DNA vaccines could be developed where cDNA is incorporated into tissues of the target host, these cells express foreign protein that the host recognizes as foreign and builds antibodies to these.

EXAMPLES

Electron Microscopy

A blister on the patient's hand was cleansed with alcohol and vesicular fluid (approx. 25 mL) was aspirated and placed into 1 mL of sterile distilled water. The sample was vortexed and clarified for 10 minutes at 850×g. The resulting supernatant was transferred to a new tube and centrifuged 20 minutes at 15,000×g. The pellet was resuspended in 10 µL of distilled water and transferred to parafilm. A Formvar-coated, 300-mesh copper grid was floated on the drop for 2 minutes, blotted dry with filter paper, stained with phosphotungstic acid (PTA), and examined at an accelerating voltage of 80 kilovolt (KV) using a Phillips 300 transmission electron microscope (EM). Subsequent to EM examination, the remainder of the sample was processed for virus isolation.

Virus Propagation

Isolation of the calicivirus SMSV5 Hom-1 was carried out in Vero cell monolayers inoculated with 0.2 ml of a 1:10 sterile distilled water dilution of vesicular fluid aspirate and then incubated and examined for cytopathic effect and isolates plaque passaged three times, as previously described [1]. For comparisons, the clinical human isolates and prototype SMSV-5 strain 205 originally isolated from an ill pinniped [1] were used for agar gel electrophoresis (SDS-PAGE) capsid protein comparisons. Vero cells were inoculated with a multiplicity of infection (MOI)>10 of the respective viruses, incubated for one hour at 37° C., then rinsed and fed with minimum essential media (MEM) plus 1% fetal bovine sera (FBS) and incubated at 37° C. At 3.5 hours post inoculation, the medium was removed, the cells rinsed once with MEM and then fed for 30 minutes with methionine-free MEM containing actinomycin D at 2 µg/ml. At 4 hours post inoculation, fresh methionine-free medium with $^{35}$S-methionine (25 µCi/ml) was added and uptake of labeled methionine was allowed to continue for 30 minutes. The cells then were rinsed once with ice-cold 0.5 M tris-HCl (pH 7.4) and samples collected with lysis buffer (0.05 M tris-HCl and 2% SDS, pH7.4). Samples were processed for immunoprecipitation and were electrophoresed under reducing conditions.

Serum Neutralization

Neutralization for typing and to determine antibody titers in patient sera were completed using Vero cells in 96 well plates and replicates of 4 wells with 2 fold dilution of test serum against 100 tissue culture infective dose (TCID)$_{50}$ of virus [1]. The human isolate was typed using twenty antibody units of heterologous typing serum from each of 40 calicivirus types including SMSV-5 [26].

ELISA for Antibody to SMSVs

Assays were completed using a 96-well microtiter plate (#76-371-04, ICN Biomedicals Inc. Horsham, Pa.) The test antigen consisted of a pool of three CsCl banded caliciviruses (SMSV-5, SMSV-13, and SMSV-17) in 0.1 M carbonate buffer, pH 9.6. The test antigen was adsorbed to the plate for 2 hours at 37° C., then washed 2× with tris buffered saline containing Tween 20 Tris buffered saline in tween (TBST) and blocked overnight at 4° C. with TBST containing 0.25% BSA. After two TBST washes, each serum diluted 1:100 in blocking buffer was added for 2 hours at 37° C., then washed 6× with TBST. Next, anti-human IgG-alkaline phosphatase (SIGMA), diluted 1:40,000 in blocking buffer, was added and incubated 2 hours at 37° C., then the wells were washed 6× with TBST and 2× with TBS without Tween. The chromogenic substrate pnpp (SIGMA) was added (200 µl per well at 1 mg/ml) and incubated overnight at 37° C. Optical densities (OD) were read at 405 nm on an enzyme linked immunosorbent assay (ELISA) plate reader (Titertek Multiskan). The OD value used was the test OD value minus the OD of a serum control well.

The OD values of control wells were 0.005, and most were 0.000. Values above an OD of 0.2 are considered positive.

RT-PCR Amplicon Generation

Amplicons (cDNA amplification products of a specific template RNA sequence) were generated by reverse transcriptase-polymerase chain reaction (RT-PCR) using primers Pr35 and Pr36 based upon the Pan-1 sequence.[9, 10] RT-PCR products were cloned into pGem-T (Promega, Madison, Wis.) and sequenced using "forward" and "reverse" primers and dideoxy chain termination. Primers PrCV35, PrCV36, and PrCV39 were synthesized from the sequence of Pan-1 (Matson D O, Zhong W-M, Jiang X, Smith A W, Unpubl.) PrCV35 and PrCV36 (nucleotides 5200–20 and 4727–45 of the Pan-1 sequence, respectively) and span GLPS and YGDD amino acid motifs characteristic of the presumed viral RNA polymerase. PrCV39 (nucleotides 5622–50 of the Pan-1 sequence) begins 46 nucleotides upstream from the first AUG in the second open reading frame (ORF) of Pan-1, the ORF that encodes the capsid protein. The primer sequences were: PrCV35, 5'-CGGGTCGGTTTCAGACCAAAC-3' (SEQ ID NO: 8); PrCV36, 5'-ATCCAAGTTGGCATCAAA-3' (SEQ ID NO: 9), and PrCV39, 5'-GTGGTCGGCCGGGGCT-CGTTGGGGAGGTG-3' (SEQ ID NO: 10). Additional internal primers were synthesized for sequencing reactions. The pGEM-T vector system (Promega Corporation, Madison, Wis.) was used to clone RT-PCR products for sequencing. One to two cDNA clones of the predicted size were sequenced with "forward" and "reverse" primers using the $^{35}$S-dideoxy nucleotide chain termination procedure (Sequenase kit, United States Biochemical Corporation, Cleveland, Ohio). Internal primers were synthesized to complete the sequencing on both strands of each clone. Radionucleotide-labeled products were resolved in 8% polyacrylamide gels that were exposed overnight to X-AR-2 film (Kodak, Rochester, N.Y.).

Method Of Creating Monoclonal Antibodies That Recognize and/or Neutralize Multiple Serotypes Of Vesiviruses The goal of creating monoclonal antibodies that recognize and/or neutralize multiple different calicivirus strains was achieved using two different methods of developing antigens. The first method involved a "surface-in" approach wherein the virions were enzymatically degraded for set periods of time and then used as antigens to inoculate mice. The second method involved infecting a cell culture with calicivirus and taking samples at various time intervals with the intent of isolating epitopes that are normally not present on the exterior of the virion. This second method is termed the "inside-out" method. Both methods offer the possibility of generating both a humoral response and a cellular immune response where intracellular calicivirus specific polypeptides of 9–11 amino acids in length could be presented via the Type I histocompatibility complex to killer T cells which in turn would lyse calicivirus infected host cells thereby arresting virus replication.

A number of epitopes associated with a neutralizing antibody response have been described for the feline calicivirus but all are type specific and between serotype neutralizing activity was not shown (*Tohya et al., 1991, Arch. Virol. 117:173–181). However, highly conserved monoclonal antibody binding epitopes on the capsid protein common to as many as 38 calcivirus serotypes (FIG. 13) has been demonstrated as well as a series of monoclonals antibodies that neutralize multiple serotypes (FIG. 12). Those with neutralizing antibody binding action give strong insight into the specific functional moieties that are present and highly conserved which are critical to caliciviral survival and/or replication. This also suggests that these important functional components are sequestered such that the immune system will preferentially select the more available, but often variable, viral epitopes. It also suggests that if humoral antibody can be successfully targeted for specific, but essential elements that are minor epitopes, then these antibodies should block critical functions and be protective.

The first method of generating calicivirus epitopes was accomplished by progressively peeling off of major epitopes on the more exposed outer surfaces of the calcivirus coat protein, using progressive digestion with specific proteolytic enzymes. This would be a "surface-in" approach. These digests were stopped at predetermined time intervals established by using direct electron microscopic (EM) examination to determine the degree of capsid degradation. The digestion products were used to produce a series of monoclonal antibodies in mice. Then mouse splenocytes from mice injected with these caliciviral digest preparations were fused with myeloma cells and fusion supernatants examined for cross neutralizing Mab. The positive results are shown in FIG. 12. These Mabs can now be reacted against polypeptides generated from a calcivirus cDNA library cloned into a high efficiency eukaryotic expression vector (pcDNA 1). Polypeptides bound by cross-reactive neutralizing Mabs can be further examined as vaccine candidates either singly or in combination.

The second method of generating calicivirus specific monoclonal antibodies involved working from the inside out, by examining viral polypeptides which occur as the replicative cycle progresses. To do this, samples of a calicivirus-infected cell culture were frozen beginning with 60 minutes after absorption to cell cultures and then every 30 to 60 minutes thereafter up to 8 hours or until replication was complete. Each time interval preparation was used as outlined above for producing mouse monoclonal antibodies that were screened for calicivurs neutralizing activity. The rationale for this "core-out" approach is to examine viral replicative proteins, such as the capsid precursor protein, non-structural proteins, genome associate protein, and similar functional antigens that might be lost or altered during virus maturation and release. Monoclonal antibodies resulting from these two series of experiments showed the ability to bind up to 38 different calicivirus serotypes (FIG. 13) and to neutralize several calicivirus serotype (FIG. 12).

RESULTS AND DISCUSSION

A. Human Subject with Flu-like Illness and Blistering

Figure 2:
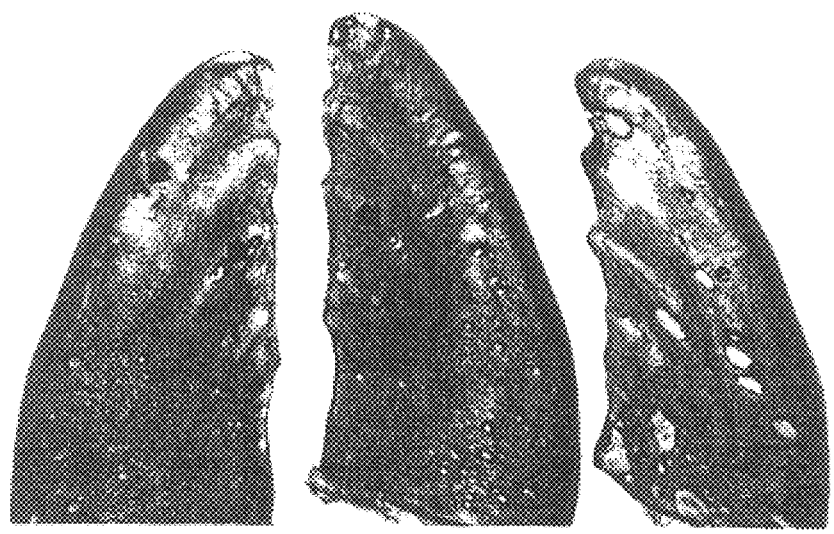
FIG. 2 is a flipper lesions on Northern fur seals from which the prototype strain (205) of SMSV-5 was isolated. Solid arrows show intact vesicles particularly around the vestigial claws and "e" shows erosions left by denuded vesicular lesions.

A 32-year-old male researcher developed a flu-like illness that was followed in two days by an initial blister on the right index finger. Within 12 hours, deep, painful blisters (not unlike hand, foot and mouth disease caused by some enteroviruses) [11] appeared on the palms and fingers of both hands (FIG. 1) and by 24 hours on the soles and toes of both feet. In all, several dozen lesions occurred, ranging from small, red, raised areas to fluid-filled blisters 1 cm in diameter. Healing commenced within 1 week and was essentially complete in 2 weeks. The prototype SMSV-5 calicivirus was isolated from similar lesions on the flippers of northern fur seals. (FIG. 2)

Figure 3:
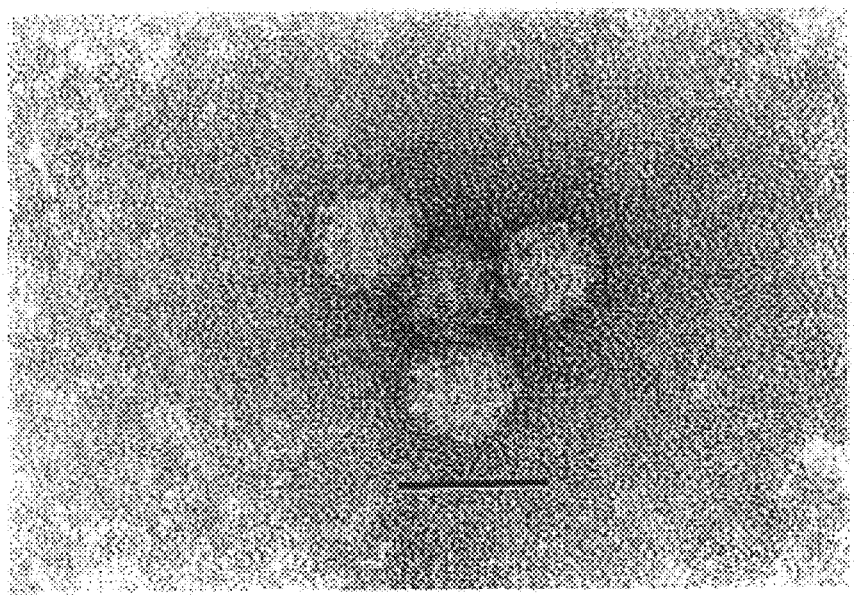
FIG. 3 is an electronphoto micrograph using phosphotungstic acid negative stain. One of several clusters of virus-like particles from human vesicular fluid having morphology characteristic of the caliciviruses (bar=50 nm).

Virus particles having the morphologic characteristics typical of the Caliciviridae were visualized by negative contrast electron microscopy in the aspirated vesicular fluid [12] (FIG. 3), and a calicivirus was isolated in Vero cells. Comparisons of RT-PCR amplicons of SMSV-5 strain 205, [1] and the virus isolate from the hand lesions revealed that these were the same genotype. (FIG. 4) [11] The human isolate, designated strain SMSV-5 *Homosapien*-1 (SMSV-5 Hom-1), was neutralized by typing antiserum to SMSV-5 but was not neutralized by typing antisera to 39 other calicivirus serotypes.

The infected individual developed type-specific neutralizing antibodies measured using 100 $TCID_{50}$ of prototype SMSV-5 of test virus as follows: the pre-exposure serum was negative at a 1:4 serum dilution. On day 4 post infection (PI), the neutralization titer was 1:10 and was 1:80 on days 28 and 180 PI. Convalescent serum (day 28 PI) immunoprecipitated the single capsid protein (60 KDa) of the prototype SMSV-5 and SMSV-5 Hom-1, but not proteins in mock-infected Vero cells. SMSV-5 typing serum also immunoprecipitated the capsid protein of both virus stocks. (Figure not shown) In addition, findings of neutralizing antibody in humans were reported previously.[1, 2]

The source and route of exposure to SMSV-5 could not be determined with certainty and additional or secondary cases were not seen. However, at the time, the infected individual was routinely processing gradient-purified prototype caliciviruses including serotype SMSV-5, working around the mouths and teeth of calves experimentally infected with SMSV-5 and isolating in cell culture the virus being shed in their oropharyngeal secretions.

B. Testing Unselected Adult Population for Antibodies to SMSVs

To determine, whether an unselected adult population had been infected with SMSVs in the past, serum reactivity was measured by ELISA using a calicivirus group antigen test. Eighteen percent of 300 sera collected from adults donating blood in Portland, Oreg. during a 6-month period in 1996 had reactivity (OD value>0.20 or 8% at OD>0.50) in an ELISA using as test antigen three CsCl banded marine calicivirus serotypes including SMSV-5. (FIG. 5). Two of two ELISA-positive samples (OD values 0.884 and 1.690) were confirmed to have antibody to the 60 KDa capsid protein of a marine calicivirus (Strain McAll) by Western blot while one ELISA-negative sample (OD 0.011) was also negative by Western blot. Fourteen serum samples (paired samples, acute and convalescent) from seven individuals with confirmed diagnoses of Norwalk gastroenteritis did not test positive against the SMSV group antigen, and the OD readings of convalescent sera compared to acute showed no detectable rise (Data not shown). For these reasons it is believed that the reactivity to SMSV antigen cannot be discounted as cross reactivity to infection from other human caliciviruses of the Norwalk group and ELISA reactivity to our calicivirus antigen could be eliminated by preadsorbing the sera with calicivirus antigen.

C. Antibodies Directed to Calicivirus are Detected in the Serum From Patients Who Suffered Spontaneous Abortions The Elisa assay discussed above was used to test serum samples from cases of spontaneous abortion. 100 samples were tested and 15% of these gave positive responses in the ELISA test. In comparison 5% of 398 samples collected from "normal" subjects were positive. Thus, establishing a link between calicivirus infection and spontaneous abortion.

D. Calicivirus Hepatitis Agent Transmitted by Blood

Five serums sets provided by the American Red Cross Regional Testing Laboratory Portland, Oreg. and Chiron Corp., Emeryville, Calif. were tested for the presence of calicivirus antibodies. The ELISA described above using a pooled vesivirus antigen made up of SMSV-5, SMSV-13, and SMSV-17 was used to test the serum. The results from these serum samples were as follows:

| GROUPS* | POSITIVE | NEGATIVE | TOTAL | % Positive |
|---|---|---|---|---|
| Normal Red Cross Serums* | 19 | 379 | 398 | 5% |
| ALT Elevated >120 But Negative For Hepatitis B And C As Well As All Other Viral Agents Routinely Tested For.* | 17 | 181 | 197 | 9% |
| Clinical Cases Of Hepatitis That Were Negative For Hepatitis A-G** | 2 | 14 | 16 | 13% |
| Positive Samples For Hepatitis B And C** | 2 | 8 | 10 | 20% |
| Clinical Cases Of Hepatitis Following Transfusion Or Dialysis** | 7 | 25 | 32 | 22% |

Chi sq. = 17.1, P = <.001
*samples provided by the American Red Cross
**samples provided by Chiron Corp.

The above groupings are rank ordered for probable risk for blood transmission (transfusion transmitted) hepatitis and the data provides compelling evidence of a calicivirus hepatitis agent transmitted via blood a P value of <0.001.

E. Antibodies Directed to Calicivirus are Detected in the Serum From Patients Who Suffer From Chronic Fatigue Syndrome The ELISA described above, which utilizes SMSV-5, -13, and McA11, to bind to vesivirus specific antibodies was used to test for the presence of vesivirus specific antibodies in serum from patients with Chronic Fatigue Syndrome (CFS). Ten control serum samples were tested and ten CFS samples were tested. The results show that at least 20% of the CFS samples had elevated levels of vesivirus specific antibodies.

| Code Number | | Sera plus antrigen | Serum Control | Corrected OD |
|---|---|---|---|---|
| 176-A | Control | .314 | .001 | .314 |
| 186-B | Control | .014 | .002 | .012 |
| 191-C | Control | .018 | .000 | .018 |
| 192-D | Control | .006 | .001 | .005 |
| 193-E | Control | .012 | .002 | .010 |
| 194-F | Control | .050 | .003 | .047 |
| 195-G | Control | .018 | .000 | .018 |
| 196-H | Control | .045 | .001 | .044 |
| 197-I | Control | .027 | .002 | .025 |
| 199-J | Control | .008 | .000 | .008 |
| 413-K | CFS | .433 | .003 | .430 |
| 478-L | CFS | .041 | .009 | .032 |
| 602-M | CFS | .017 | .007 | .010 |
| 644-N | CFS | .102 | .003 | .099 |
| 712-O | CFS | .049 | .005 | .044 |
| 718-P | CFS | .276 | .001 | .275 |
| 787-Q | CFS | .012 | .005 | .007 |
| 805-R | CFS | .011 | .004 | .007 |
| 1184-S | CFS | .036 | .012 | .024 |
| 1206-T | CFS | .018 | .010 | .008 |

F. Additional Diseases That May Be Associated With Calicivirus Infection In Humans The discovery that calicivirus is an infectious agent in humans makes it likely that other diseases in humans will be linked to calicivirus infection. Moreover, it is likely that humans may suffer from similar diseases as those that are already known to be caused by calicivirus in other mammals. The following table shows which diseases have previously been shown to be associated calicivirus infections in various species.

nia's marine populations are believed to have been the origins of the historic nationwide epizootic of vesicular exanthema of swine (VES) [13, 14]. The feeding of raw or poorly cooked fish products is the recognized mechanism whereby these "ocean" caliciviruses were introduced into terrestrial mammals [13]. Once VES was established in swine, then pork scraps from these infected pigs were discarded into garbage and fed to others thereby initiating a devastating pig-to-pig disease cycle [13, 14]. These historical events involving caliciviruses of ocean origin are not unlike the current Bovine Spongiform Encephalopathy (BSE) cycle in which cattle were thought to have been originally infected by some other species (Scrapie in sheep) and then bovine tissues containing the BSE agent were fed to cows resulting in an epidemic of BSE among cattle [15].

An animal calicivirus of ocean origin, having ocean reservoirs involving cycles through marine invertebrates, poikilotherms and mammals, now is shown to be a human pathogen. This is a new paradigm for disease occurrence and the history of this previously unknown zoonotic virus cycle is as follows: Caliciviruses of ocean origin were first isolated in primate and human cell lines [1], exposed laboratory workers developed type-specific neutralizing antibodies [2, 13], and the host range of single serotypes included species as phylogenetically diverse as fish, seals, swine and primates therefore suggesting host non specificity that could extend to humans [13]. Three serotypes (SMSV-4, SMSV-5, and VESV-$C_{52}$) induced vesicular lesions at inoculation sites in monkeys [2]. Primate calicivirus (PCV-Pan-1) is in the marine calicivirus genogroup and was recovered from five species of nonhuman primates, including two species of great apes (pygmy chimpanzee *Pan paniscus* and lowland gorilla *Gorilla gorilla*) [10,13,16,17]. In one species (pygmy

| DISEASE CONDITION | SPECIES | | | | | | | | |
|---|---|---|---|---|---|---|---|---|---|
| | SWINE | HORSE | CAT | COW | SHEEP | DOG | PINNIPED | CETACEAN | PRIMATE |
| Blistering and Erosion of Mucus Membranes | X | | X | | X | | | | X |
| Pneumonia | | | X | X | | | X | | |
| Diarrhea | X | | | X | | X | | | X |
| Myocarditis | X | | | | | | X | | |
| Myositis | | | X | | | | | | |
| Hepatitis | X | | | | | | | | |
| Encephalitis | X | | | | | | X | | X |
| Abortion | X | | X | | | | X | | |
| Hemorrhage | X | | | | | | X | | |
| Vesicles | X | X | X | X | | X | X | X | X |
| Thymic Involution | | | | | | | X | | |

Ten (10) Disease Conditions Expected in Humans By Either Using Extrapolation from Animal Models or Direct Evidence in Either Humans or Primates.

G. Summary Of Results

SMSV-5 was recovered originally in 1973 from a vesicle on the flipper of a severely affected northern fur seal (*Callorhinus ursinus*) necropsied on St. Paul Island, Ak. [1] (FIG. 2). Altogether, more than 21 other calicivirus serotypes have been isolated from marine mammals and some of these also have been isolated from domestic livestock [13], further evidence of "viral traffic" between marine and terrestrial species is shown in terrestrial animals by the presence of type specific serum antibodies to a variety of marine calicivirus serotypes[13]. In retrospect, caliciviruses circulating in the 1930's, 1940s, and 1950's in southern Califorchimpanzee), the virus was recovered from a herpesvirus-like lip lesion and was excreted in oropharyngeal secretions for at least six months [10]. Another PCV Pan-1 isolate was recovered from the brain of a baby douc langur (*Pygathrix nemaeus*) which died with encephalitis [16].

There have been occasional field reports of unusual blistering skin infections among wildlife biologists working with pinnipeds (Personal communication, Robert L. DeLong, National Marine Mammal Laboratory, Sand Point, Seattle, Wash., 1994). One individual who handled diseased Steller sea lions (*Eumetopias jubatus*) in the Bering Sea required emergency medical treatment for deep, painful blistering of the hard palate, upper lip and facial area. Although the attending physician made a clinical diagnosis of herpesvirus infection, throat washings taken 30 days post onset produced a calicivirus isolate, (currently designated strain McAll). This virus was not neutralized by the 40 different type-specific antisera available at the Laboratory for Calicivirus Studies and will be designated a new calicivirus type. Serum samples were collected at 30, 45 and 60 days post onset. Only the 30-day sample was positive using ELISA with the McAll virus as antigen. Preliminary sequence data indicates this isolate is in the same genogroup as the SMSVs of ocean origin, (Unpublished data, Smith, A W, Skilling, D E, Matson, D O, and Berke, T.) thereby providing evidence of a second, although not fully documented, case of zoonotic calicivirus disease.

SMSV-5 is one of 40 cultivatable calicivirus serotypes. Subtypes include additional marine and closely related strains isolated from terrestrial animals. All appear to share a common genomic organization [11, 18]. Many serotypes replicate in feline, canine, pig, primate and human cell lines [19] and their similar genomic organization, close sequence identity, and common replicative properties in host animals and cell cultures suggest that SMSV-5 is only one of many calicivirus serotypes in the marine genogroup that could be expected to infect humans if exposure occurs [2]. In fact, the untyped SMSV isolate recovered from the biologist and designated strain McAll, the high levels of neutralizing antibody to serotype SMSV-4 in humans and the presence of antibodies to SMSVs in blood donors living in the pacific rim are three additional pieces of evidence which suggests that this has occurred [2].

This disclosure describes a newly recognized human disease produced by a novel strain of calicivirus, SMSV-5 Hom-1. The apparent viremia with dissemination of virus to multiple sites of replication on all four extremities mimics the disease observed in pinnipeds and swine infected with the same and related serotypes [1,13, 14, 20]. Pneumonitis, myocarditis, encephalitis, hemorrhagic disease or disseminated intravascular coagulation, gastroenteritis, hepatitis, blistering and reproductive disorders with secondary and cross-species transmission, involving reptiles, amphibians, primates and other mammals, have been described in association with calicivirus infections in animals [2,13,19–22]. In humans, caliciviruses are known to cause gastroenteritis and hepatitis and now blistering [23–25]; however, improved diagnostic methods and an understanding of this newly recognized virus cycle should provide insight for the future diagnosis of additional human diseases for which an etiology is currently unknown.

The above embodiments are set out only as examples and are no way meant to limit the scope of the invention claimed which is to be interpreted only in view of the claims.

It should be apparent to one skilled in the art that the invention described herein can be modified in arrangement and detail without departing from the scope or spirit of the invention and the claims encompass all such modifications.

REFERENCES

*1. Smith A W, Prato C M, Skilling D E. Characterization of two new serotypes of San Miguel sea lion virus. *Intervirology* 1977; 8: 30–36.

*2. Smith A W, Prato C M, Skilling D E. Caliciviruses infecting monkeys and possibly man. *Am J Vet Res* 1978; 39: 287–289.

*3. Sexton D J, Rollin P E, Breitschwerdt E B, Corey G R, et al. Life threatening Cache Valley virus infection. *New Eng J of Med* 1997;336: 547–549.

*4. Murray K, Selleck P, Hooper P. et al. A morbillivirus that caused fatal disease in horses and humans. *Science* 1995; 268, 94–97.

*5. Morse S S. Examining the origins of emerging viruses. "In" Emerging Viruses, ed. Morse, S. S., Oxford University Press, London, N.Y. 1993; p.10–28.

*6. Liu S J, Xue H P, Pu B Q, et al. A new viral disease in rabbits *Anim Husb Vet Med* 1984; 16: 253–255.

*7. Xu Z J and Chen W X. Viral haemorrhagic disease in rabbits: a review. *Vet Res Commun*. 1989; 13: 205–212.

*8. Chasey D, Lucas M H, Westcott D G, et al. Development of a diagnostic approach to the identification of rabbit hemorrhagic disease. *Vet Rec* Aug. 12, 1995; 137:158–160.

*9. Smith A W, Skilling D E, Ensley P K, Benirschke K and Lester T L. Calicivirus isolation and persistence in a pygmy chimpanzee (*Pan paniscus*). Science 221, 79–81.

*10. Matson D O, Berke T, Dinulos M B, et al. Partial characterization of the genome of nine animal caliciviruses. *Archives of Virol* 1996; 141, 2443–2456.

*11. Melnick J L. Enteroviruses—Hand Foot, and Mouth Disease. In: Fields Virology, 2nd ed. Vol. 1. Raven Press, New York, 1990; p.565.

*12. Skilling D E, Barlough J E, Berry E S and Smith A W. A simple, rapid method for preparation of virus isolates from cell culture for electron microscopy. *J. Tissue Cult. Meth*. 1985; 9, 217–220.

*13. Smith A W and Boyt P. Caliciviruses of ocean origin: a review. *J of Zoo and Wildlife Medicine* 1990; 21, 3–23.

*14. Bankowski R A. Vesicular exanthema. In: Bankowski, R. A. (Ed.) Advances in Veterinary Science. Academic Press 1965; New York; 23–64.

15. Westaway B, Carlson G A and Prusiner S B. On safari with PrP: prion diseases of animals. *Trends Microbiol*. 1995; 3:141–147.

*16. Smith A W, Skilling D E, Anderson M P and Benirschke K. Isolation of primate calicivirus *Pan paniscus* type-1 from a douc langur (*Pygathrix nemaesus* 1.). *J. Wildl. Dis*. 1985; 21, 426–428.

*17. Smith A W, Skilling D E and Benirschke K. Calicivirus isolation from three species of primates: an incidental finding. *Am. J. Vet. Res*. 1985; 46, 2197–2199.

*18. Neill J D, Meyer R F and Seal B S. Genetic relatedness of the caliciviruses: San Miguel sea lion and vesicular exanthema of swine viruses constitute a single genotype within the Caliciviridae. *J of Virol*, 1995; 69, 4484–4488.

*19. Smith A W, Madin S H, Vedros N A and Bankowski R A. Host range comparisons of five serotypes of caliciviruses. AJVR 1977;38:101–5.

*20. Smith A W, Skilling D E, Dardiri A H and Latham A B. Calicivirus pathogenic for swine: a new serotype isolated from opaleye *Girella nigricans*, an ocean fish. *Science* 1980; 209, 940–941.

*21. Poet S E, Skilling D E, Megyesi J L, Gilmartin W G and Smith A W. Detection of a non-cultivatable calicivirus from the white tern (*Gygis alba rothschildi*). *J. Wildl. Dis*. 1996; 32, 461–467.

*22. Smith A W, Akers T G, Madin S H and Vedros N A. San Miguel sea lion virus isolation, preliminary characterization and relationship to vesicular exanthema of swine virus. *Nature* 1973; 244, 108–110.

23. Waxham M N and Wolinsky J S. Immunochemical identification of rubella virus hemagglutin. *Virology* 1983; 126, 194–203.

*24. Matson D O, Zhong W M, Nakata S, et al. Molecular characterization of a human calicivirus with closer genetic relationship to feline caliciviruse than other human caliciviruses *J. Med. Virol.* 1995; 45, 215–222.

*25. Bradley D W. Hepatitis E virus: a brief review of the biology, molecular virology, and immunology of a novel virus. *J. Hepatol.* 1995; 22, 140–145.

*26. Smith A W, Berry E S, Skilling D E, Barlough J E, Poet S E, Berke J, and Maston D O. In vitro isolation and characterization of a calicivirus causing a vesicular disease of the hands and feet. Clinical Infectious Diseases 1998; 26: 434–439.

The references that are preceded by an asterisk * are herein incorporated by reference.

What is claimed is:

1. A purified protein isolated from calicivirus, comprising:

(a) an amino acid sequence encoded by SEQ ID NOS: 11, 12, or 13;

(b) an amino acid sequence that differs from the amino acid sequence specified in (a) by one or more conservative amino acid substitutions while retaining at least one epitope of the amino acid sequence specified in (a); or (c) an amino acid sequence having at least 80% sequence identity to the amino acid sequence specified in (a) while retaining at least one epitope of the amino acid sequence specified in (a), and wherein the purified protein is capable of being used to detect calicivirns infection in humans.

2. A method of detecting calicivirus antibodies in a human, the method comprising:

obtaining a tissue sample from a human who is suspected of suffering from a disorder selected from the group consisting of diarrhea, myocarditis, myositis, encephalitis, hemorrhage, vesicles, pneumonia, blistering and erosion of mucosal membranes, thymic involution, chronic fatigue syndrome, hepatitis, and spontaneous abortion;

contacting the tissue sample from the human with at least one calicivirus epitope comprising a purified protein according to claim 1, or a fragment thereof, that retains the at least one calicivirus epitope; and detecting antibody bound to the epitope, the detection of antibody bound to the epitope indicating the presence of calicivirus antibodies in the human.

3. The method of claim 2, wherein the human has hepatitis symptoms, has chronic fatigue syndrome, or has had a spontaneous abortion.

4. The method of claim 2, wherein the epitope is found in SMSV-5 Hom-1 (ATCC No. PTA-4762).

5. An immunostimulatory polypeptide, comprising:

a polypeptide having a sequence according to SEQ ID NO: 5 or a fragment thereof containing at least one epitope from the polypeptide having a sequence according to SEQ ID NO: 5; or a polypeptide encoded by the amino acid sequence of SEQ ID NO: 11, 12, or 13, or a fragment thereof containing at least one epitope from the polypeptide encoded by the amino acid sequence of SEQ ID NO: 11, 12, or 13, wherein the polypeptide is capable of being used to detect calicivirus infection in humans.

6. A method of detecting calicivirus antibodies in a human, the method comprising:

obtaining a tissue sample from a human who is suspected of suffering from a disorder selected from the group consisting of diarrhea, inyocarditis, myositis, encephalitis, hemorrhage, vesicles, pneumonia, blistering and erosion of mucosal membranes, thymic involution, chronic fatigue syndrome, hepatitis, and spontaneous abortion;

contacting the tissue sample from the human with at least one calicivirus epitope comprising an immunostimulatory polypeptide according to claim 5; and detecting antibody bound to the epitope.

7. The method of claim 6, wherein the human has hepatitis symptoms, has chronic fatigue syndrome, or has had a spontaneous abortion.

8. The method of claim 6, wherein the epitope is found in SMSV-5 Hom-1 (ATCC No. PTA-4762).

9. An isolated polypeptide comprising the amino acid sequence shown in SEQ ID NO: 5.

10. A purified protein isolated from calicivinis, comprising:

(a) an amino acid sequence according to SEQ ID NO: 5;

(b) an amino acid sequence that differs from SEQ ID NO: 5 by one or more conservative amino acid substitutions while retaining at least one epitope of SEQ ID NO: 5; or (c) an amino acid sequence having at least 90% sequence identity to SEQ ID NO: 5 while retaining at least one epitope of SEQ ID NO: 5, and wherein the protein is capable of being used to detect calicivirus infection in humans.

11. A method of detecting calicivirus antibodies in a human, the method comprising:

obtaining a tissue sample from a human who is suspected of suffering from a disorder selected from the group consisting of diarrhea, myocarditis, myositis, encephalitis, hemorrhage, vesicles, pneumonia, blistering and erosion of mucosal membranes, thymic involution, chronic fatigue syndrome, hepatitis, and spontaneous abortion;

contacting the tissue sample from the human with at least one calicivirus epitope comprising a purified protein according to claim 10, or a fragment thereof, that retains the at least one calicivirus epitope; and detecting antibody bound to the epitope.

12. The method of claim 11, wherein the human has hepatitis symptoms, has chronic fatigue syndrome, or has had a spontaneous abortion.

13. The method of claim 11, wherein the epitope is found in SMSV-5 Hom-1 (ATCC No. PTA-4762).

* * * * *